United States Patent
Cui et al.

(10) Patent No.: US 6,726,818 B2
(45) Date of Patent: Apr. 27, 2004

(54) BIOSENSORS WITH POROUS CHROMATOGRAPHIC MEMBRANES

(75) Inventors: Gang Cui, Younkil-si (CN); Jae Hyun Yoo, Seoul (KR); Byung Wook Woo, Seoul (KR); Moon Hwan Kim, Buchun-si (KR); Hyun Joon Oh, Seoul (KR); Hakhyun Nam, Seoul (KR); Geun Sig Cha, Seoul (KR)

(73) Assignee: i-Sens, Inc., Seoul (KR)

( * ) Notice: Subject to any disclaimer, the term of this patent is extended or adjusted under 35 U.S.C. 154(b) by 104 days.

(21) Appl. No.: 09/904,930

(22) Filed: Jul. 13, 2001

(65) Prior Publication Data

US 2002/0027072 A1 Mar. 7, 2002

(30) Foreign Application Priority Data

Jul. 21, 2000 (KR) .......................... 2000-41962
May 18, 2001 (KR) .......................... 2001-27117

(51) Int. Cl.$^7$ ............................................ G01N 27/327
(52) U.S. Cl. ....................... 204/403.01; 204/403.1; 204/403.11; 204/403.14
(58) Field of Search .............. 204/403.01, 403.02, 204/403.04, 403.07, 403.11, 403.14, 403.1

(56) References Cited

U.S. PATENT DOCUMENTS

| | | | | |
|---|---|---|---|---|
| 5,264,103 A | * | 11/1993 | Yoshioka et al. | ............ 205/778 |
| 5,922,188 A | | 7/1999 | Ikeda et al. | |
| 6,248,596 B1 | * | 6/2001 | Durst et al. | ................ 436/518 |
| 6,287,451 B1 | * | 9/2001 | Winarta et al. | .......... 205/777.5 |
| 6,309,526 B1 | * | 10/2001 | Fujiwara et al. | ........ 204/403.14 |

FOREIGN PATENT DOCUMENTS

WO    WO 98/44342    * 10/1998

OTHER PUBLICATIONS

An article entitled, "Differential Thick–Film Amperometric Glucose Sensor with an Enzyme–Immobilized Nitrocellulose Membrane", By Gang Cui et al., Electroanalysis 2001, 13, No. 3, pp. 224–228.

An article entitled, "A Disposable Amperometric Sensor Screen Printed on A Nitrocellulose Strip . . . ", By Gang Cui et al., Analytical Chemistry, vol. 72, No. 8, Apr. 15, 2000, pp. 1925–1929.

An article entitled, "Disposable Amperometric Glucose Sensor Electrode With Enzyme–Immobilized Nitrocellulose Strip", By Gang Cui et al., Chemical Sensor Research Group, Department of Chemistry, Kwangwoon Univ., pp. 1–21.

* cited by examiner

Primary Examiner—Kaj K. Olsen
(74) Attorney, Agent, or Firm—Bachman & LaPointe, P.C.

(57) ABSTRACT

Disclosed is a porous membrane built-in biosensor comprising (a) at least one substrate; (b) an electrode layer patterned on the substrate, consisting of an electrode system and a circuit connector; (c) an insulator, formed on parts of the electrode layer, for electrically separating the electrode system from a circuit connector; and (d) a porous membrane via the insulator on the electrode system, wherein, when a whole blood sample is introduced to the biosensor, the whole blood sample is separated into its components during the chromatographic motion through the porous membrane so that only blood plasma can be contacted with the electrode system. The porous membrane built-in biosensor is provided with a sample inlet, which allows samples to be introduced in a constant quantity to the biosensors porous membranes without pretreatment.

27 Claims, 21 Drawing Sheets

BIOSENSORS WITH POROUS CHROMATOGRAPHIC MEMBRANES

FIELD OF THE INVENTION

The present invention relates to biosensors with porous membranes comprising (a) at least one substrate;

(b) an electrode layer patterned on the substrate, consisting of an electrode system and a circuit connector;

(c) an insulator, for separating the electrode system and a circuit connector formed on parts of the electrode layer;

(d) a porous membrane covered with the surface of the electrode system by the insulator; and (e) a protective membrane for protecting the porous membrane, formed on the porous membrane, or upper substrate containing a sample inlet for protecting the porous membrane as well as being introducible samples wherein, when a whole blood sample is introduced to the biosensor, the whole blood sample is separated into its components during the chromatographic motion through the porous membrane so that only blood plasma can be contacted with the electrode system.

BACKGROUND OF THE INVENTION

Periodical monitoring of blood glucose levels is needed for the diagnosis and prophylaxis of diabetes mellitus. Adopting colorimetry or electrochemistry as their operation principle, strip type analyzers are conventionally used to determine glucose levels in blood.

Such a calorimetric principle is based on the glucose oxidase-colorimetric reaction represented by the following reaction formula 1:

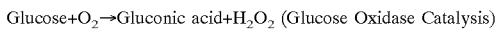

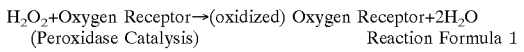

In the presence of oxygen, as illustrated in the above formulas, glucose is oxidized with the aid of glucose oxidase to produce gluconic acid and hydrogen peroxide. From the hydrogen peroxide, oxygen molecules are transferred to an oxygen receptor (chromophore) by the catalysis of peroxidase. As a result of the oxidation, the chromophore changes color, and its color intensity is the basis of the quantitative analysis of blood glucose levels.

In order to utilize this calorimetric principle, however, precise care must be taken as to sample transport, pre-treatment, quantity, reaction time, and coloration starting time. In addition, blood coagulation or various interfering materials, including uric acid, ascorbic acid and bilirubin, may disturb the calorimetric analysis. Furthermore, the accompanying photometry has the fundamental limitation that its analytical accuracy and precision is lowered at high and low concentrations of samples. With these problems, the calorimetric analysis is known to be inappropriate for accurate quantification.

To avoid the problems that the calorimetric analysis has, electroanalytical methods were chemistry was introduced to biosensors. Over the calorimetric biosensors, the electrochemical biosensors have the advantage of being higher in selectivity and sensitivity, being able to measure the colored or turbid samples, without pre-treatment, and being able to perform accurate analysis within a short period of time. In order to better understand the background of the invention, the electroanalytical chemistry on which the second-generation biosensor will be described in conjunction with the following formula 2 and FIG. 1. In contrast to the first-generation biosensor which uses oxygen as an electron transfer mediator, the second-generation biosensor takes advantage of an electron transfer mediator selected from the group comprising ferrocene, ferrocene derivatives, quinones, quinone derivatives, organic conducting salts, and viologen.

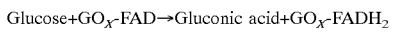

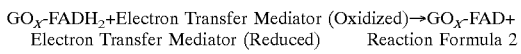

In Reaction Formula 2, $GO_X$ represents glucose oxidase, and $GO_X$-FAD and $GO_X$-FADH$_2$ are the oxidized and reduced forms of the glucose oxidase, respectively, because FAD (flavin adenine dinucleotide) is the active site of glucose oxidase. In FIG. 6, there is an electron transfer system for the electrochemical analysis of blood glucose levels, in which glucose oxidase and ruthenium are used as electron carriers from glucose to an electrode. Glucose is oxidized to gluconic acid by the catalytic action of glucose oxidase while the active site, FAD, of the glucose oxidase is reduced to FADH$_2$, which transfers its electron, in turn, to the electron transfer mediator while being returned to the oxidized form FAD. The reduced electron transfer mediator ruthenium is diffused to the surface of an electrode. At the surface of the electrode, measured is the current generated when the oxidation potential of the reduced electron transfer mediator is applied. The oxidation potential is in the range of −0.2 to 0.2 V versus a reference electrode, so that the influence of ascorbic acid and uric acid, which have oxidation potentials higher than 0.3 V and 0.4 V, respectively, can be excluded.

In contrast to the first-generation biosensor, therefore, the second-generation biosensor is not affected by oxygen. In addition, the second-generation biosensor enables the non-selective catalysis of an oxidase and uses an electron transfer mediator, which has such appropriate redox potentials as to reduce the error caused by interfering materials, so that the measured potentials can be used to accurately determine the analytical quantity of interest. However, problems are also found in the second-generation biosensor. Because the electron transfer mediator, after the electron transfer to and from the oxidase, must diffuse to the surface of the electrode to detect the electrochemical change, a large quantity of the electron transfer mediator is needed. The abundance of the electron transfer mediator may alter the three-dimensional structure of the oxidase, resulting in a decrease in the activity of the enzyme. Another problem with most electron transfer mediators is high reactivity with electrode-activating materials in the blood.

Most of the glucose sensors, which are commercially available to date, follow the principle of the second-generation biosensors. Since the electron transfer mediators employed in most commercially available glucose sensors to be oxidized at potentials similar to oxidation potentials of the interfering materials within blood, such as ascorbic acid, acetaminophene and uric acid, the influence of the interfering materials within blood is not completely eliminated. To circumvent these problems, some commercially available glucose sensors take advantage of capillarity in introducing blood samples thereinto, but suffer from the disadvantage that their fabrication is complicated because there is required the process of coating hydrophilic polymers onto hydrophobic supports to achieve the introduction.

Recently, intense attention has been paid to the use of immunochromatographic methods in biosensors. In an immunochromatographic biosensor, a porous membrane is provided to form an electrode in its upper part and a sample pretreatment layer in its lower part. Without additional operations for pretreatment, the sample was moved through chromatographic action, during which a target material of the sample can be quantitatively determined by the change in electrical quantity of the target material (Cui, G., Kim, S. J., Choi, S. H., Nam, H., Cha, G. S, and Paeng, K. J., *Anal. Chem.*, 2000, 72, 1925–1929; Cha, G. S. et al., U.S. App. Ser. No. 09/381788 now U.S. Pat. No. 6,210,907; Farm, M. L., Rorad, O. H., Park, H., International Pat. WO 00/00827 2000). It is, however, difficult to introduce an electrode and a pretreatment layer together to a porous membrane for chromatographic motion. To relieve the difficulty, an electrode is formed on a plastic substrate while a porous membrane is used for a sample introducing part. This technique, however, is disadvantageous in that the electrode does not adhere well to the porous membrane of the sample introducing part that the sensor is poor in reproducibility. Additionally, it takes a long period of time for a sample to travel through the pretreatment layer to the sensor such that the immunochromatographic biosensor, which composed of a sample pretreatment layer in its lower part, suffers from the disadvantage of requiring a long time for analysis.

To circumvent the problems encountered above, the present inventors offered a biosensor having a structure in which a porous membrane capable of chromatographically separating blood cells and blood plasma is positioned on an electrode while being pressurized against the electrode by a cover (KR 10-2000-041962). This biosensor is advantageous in that a ruthenium based electron transfer mediator is deposited on the porous membrane to lower the oxidation potential, thereby reducing the error attributable to interfering material. Also, this porous membrane-built-in biosensor enjoys the advantage of significantly reducing errors attributable to blood cell/blood plasma ratios and to easily oxidized materials. Another advantage of this biosensor resides in its structure, which has immobilized enzymes and electrode-active materials intercalated between two closed boards and thus isolated from external air, so that their lifetime can be prolonged without using separate packages. However, a serious problem with this biosensor is to make it difficult to introduce viscous blood samples thereinto.

SUMMARY OF THE INVENTION

Leading to the present invention, the intensive and thorough research on biosensors, conducted by the present inventors, a biosensor comprises: (a) at least one substrate; (b) an electrode system, formed on one end of the substrate, having a sensing material; (c) an insulator, formed on parts of the electrode layer, for electrically separating the electrode system from a circuit connector; (d) a porous membrane, covered with the surface of the electrode system, having an oxidase and an electron transfer mediator; and (e) a protective membrane as large as the porous membrane and/or an upper substrate equipped with a sample inlet, are laminated in sequence, can filter samples chromatographically through the pores of the porous membrane, be preserved for a long period of time because the sensor materials and porous membrane are closed by the upper substrate, and conduct maximum performance without being disturbed by interfering components of samples. In addition, it is found that the biosensor structure can introduce samples at constant rates to the electrodes without pretreatment, to quantify levels of samples rapidly, and to sense changes in sample level with high consistency. Further to these, the biosensors are found to allow patients to detect blood levels of metabolites associated with various diseases accurately irrespective of interfering materials and by themselves.

Therefore, it is an object of the present invention to provide a biosensor which composes: (a) at least one substrate; (b) an electrode system, formed on one end of the substrate, having a sensing material; (c) an insulator, formed on parts of the electrode layer, for electrically separating the electrode system from a circuit connector; (d) a porous membrane, formed on the electrode system, having an oxidase and an electron transfer mediator; and (e) a protective membrane for protecting the porous membrane.

It is another object of the present invention to provide a biosensor composing: (a) a substrate; (b) an electrode system, formed on one end of the substrate, having a sensing material; (c) an insulator, formed on parts of the electrode layer, for electrically separating the electrode system from a circuit connector; (d) a porous membrane, formed on the electrode system, having an oxidase and an electron transfer mediator; (e) a second electrode pattern formed on the porous membrane, facing the electrode pattern; and (f) an upper substrate, formed on the adhesive, for protecting the biosensor, having a hole through which samples are introduced inside the biosensor It is another object of the present invention to provide a biosensor with a modified sample inlet capable of rapidly introducing a predetermined amount of blood samples and increasing accuracy and reproducibility.

BRIEF DESCRIPTION OF THE DRAWINGS

The application of the preferred embodiments of the present invention is best understood with reference to the accompanying drawings, wherein like reference numerals are used for like and corresponding parts, respectively.

FIG. 2b is a perspective view showing the differential flat type biosensor of FIG. 2a;

FIG. 3b is a perspective view showing the differential face-to-face type biosensor of FIG. 3a;

FIG. 5b is a cross sectional view, taken along the line A–A' of FIG. 5a;

FIG. 8b is a cross sectional view, taken along the line A–A' of FIG. 8a;

FIG. 10b is a cross sectional view, taken along the line A–A' of FIG. 10a.

Figure 1:
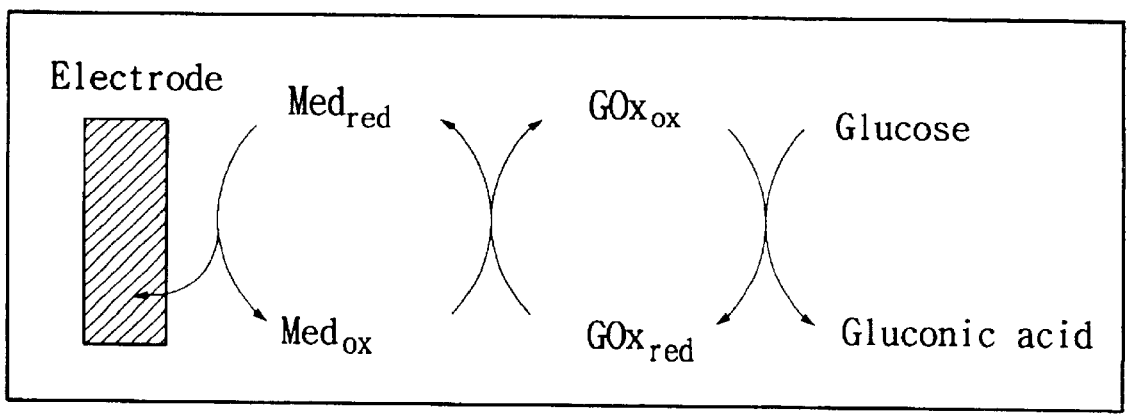
FIG. 1 is a diagram illustrating reaction mechanism between an oxidase and an electron transfer mediator on an electrode of a biosensor.

9: plurality of spaced first circuit connectors
9': second circuit connectors
10: lower substrate
11: working electrode
12: counter electrode
13: reference electrode
14: sample inlet
15: insulator
16: porous membrane
17: adhesive
18: hole of upper substrate
19: pretreatment layer
20: electrode connector
21: sample
22: protective membrane
10': upper substrate
10": second upper substrate
11': working electrode connector
12': counter electrode connector
13': reference electrode connector
15': second insulator
18': second hole of upper substrate
90: plurality of differential circuit connectors
90': second differential circuit connector
100: differential substrate
110: differential working electrode
120: differential counter electrode
130: differential reference electrode
150: differential insulator
150': differential second insulator
160: differential porous membrane
170: differential adhesive
220: differential protective membrane

DETAILED DESCRIPTION OF THE INVENTION

The application of the preferred embodiments of the present invention is best understood with reference to the accompanying drawings, wherein like reference numerals are used for like and corresponding parts, respectively.

With reference to FIG. 2, there is shown as a differential flat type biosensor with a three-compartment electrode.

As seen in these views, the differential flat type biosensor of the present invention comprises: (a) a lower substrate 10; (b) a plurality of first spaced circuit connector 9; formed on the lower substrate 10, (c) three-electrode system consisting of a working electrode 11, a counter electrode 12, and a reference electrode 13, all electrodes being established on the circuit connectors at a predetermined region (d) an insulator 15 covering the surface of the lower substrate 10 except said the electrode system and plurality of spaced first circuit connectors exposed on terminal region of the lower substrate 10; (e) a porous membrane 16, formed on the exposed area of the electrode system, having the same dimension as the exposed area of the electrode system; and (f) an protective membrane 22 large enough to cover the intermediate membrane for protecting porous membrane 16 via an adhesive 17 which is not applied to the electrode system, (g) plurality of differential circuit connectors 90 formed below the lower substrate 10; (h) a differential electrode system consisting of a differential working electrode 110, a differential counter electrode 120, and a differential reference electrode 130; (i) a differential insulator 150; (j) a differential porous membrane 160; (k) a differential adhesive 170 covering the resulting structure with the exception of the porous membrane; and (l) a differential protective membrane 220; each of the differential component, established on symmetry with respect to the lower substrate 10, which functions in the same pattern as that of its corresponding one in the opposite module.

In another embodiment of the present invention, there is provided a differential flat type biosensor with a two-electrode system, which is the same structure as previously described a differential flat type biosensor with a three-electrode system with exception that the electrode system is composed of a working electrode and a counter electrode.

Figure 3A:
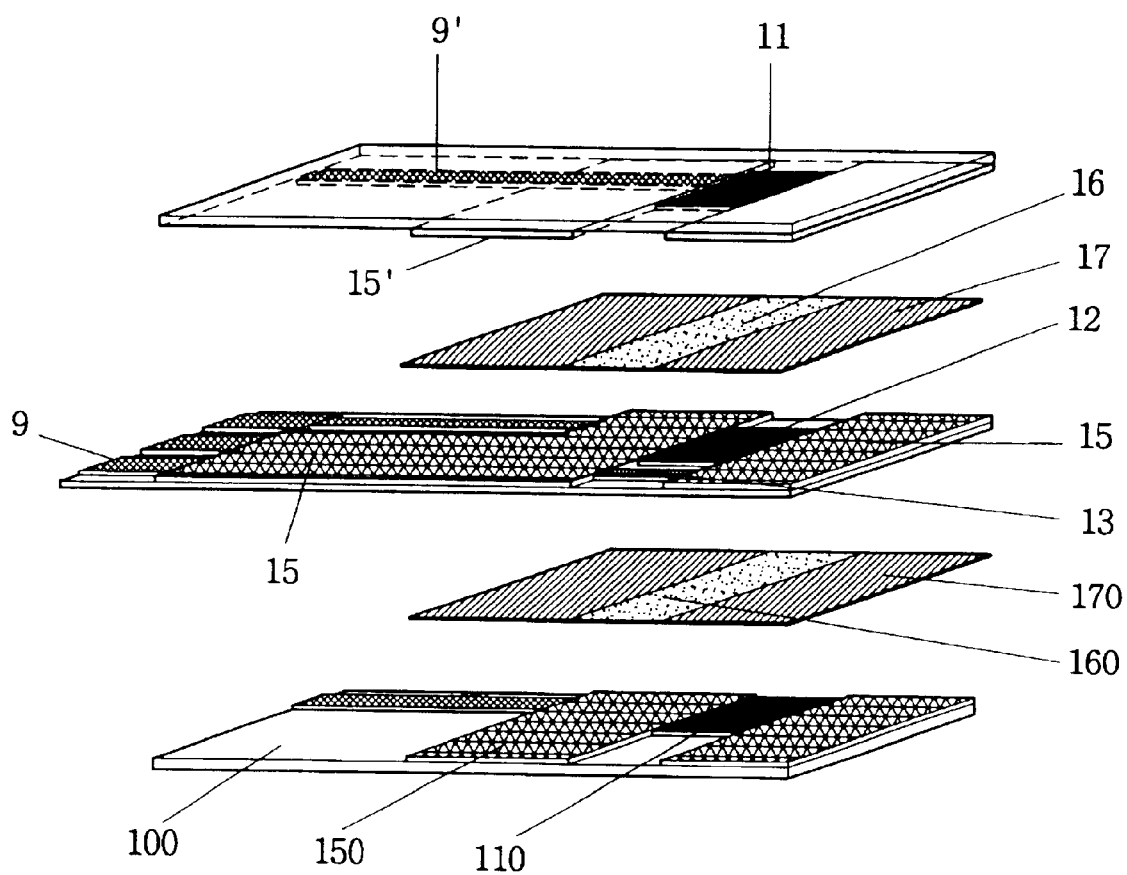
FIG. 3a is an exploded perspective view showing a differential face-to-face type biosensor adopting a three-electrode system, in accordance with a second embodiment of the present invention.
Figure 3B:
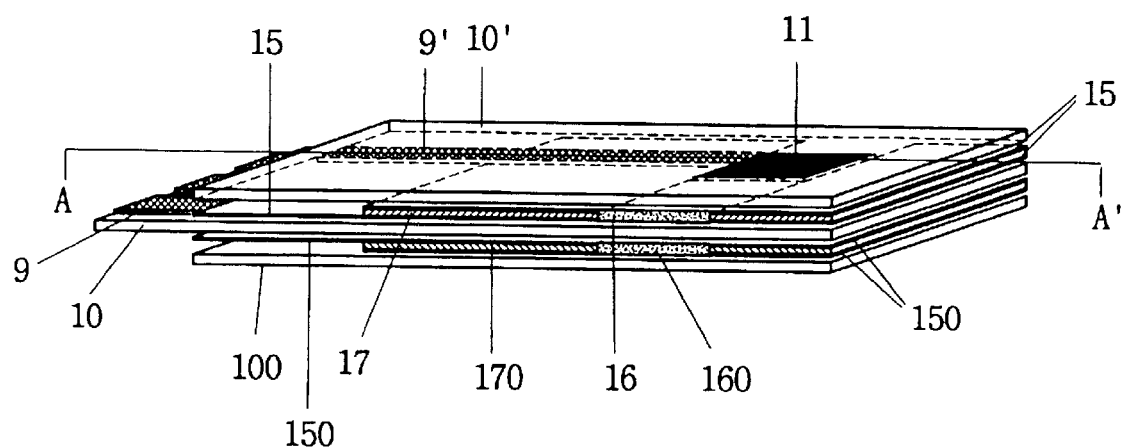
Figure 3C:
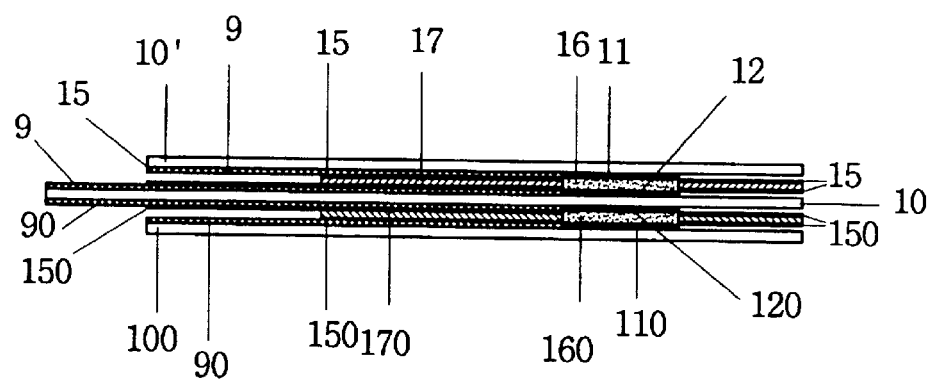
FIG. 3c is a cross sectional view, taken along the line A–A' of FIG. 3b.

It is fabricated a differential flat type biosensor that onto the porous membrane 16 are fixed glucose oxidase and an electron transfer mediator, and the differential porous membrane 160 is immobilized along with bovine serum albumin:

With reference to FIG. 3, there is shown as a differential face-to-face type biosensor with a three-electrode system.

As seen in these figures, the differential face-to-face type biosensor with three-electrode system comprises: (a) a lower substrate 10; (b) a plurality of spaced first circuit connector 9; formed on the lower substrate 10, (c) a counter electrode 12 and a reference electrode 13, both being coated on the circuit connectors 9 at a predetermined region; (d) an insulator 15 covering the surface of the lower substrate 10 exception of the electrode system containing a counter electrode 12 and a reference electrode 13; and plurality of spaced first circuit connectors 9 exposed on terminal region of the lower substrate 10; (e) a porous membrane 16 located on the electrode system containing a counter electrode 12 and a reference electrode 13, having the same dimension as the exposed area of the electrode system with a counter electrode 12 and a reference electrode 13; (f) an adhesive 17 deposited over the exception of the porous membrane 16, fixing the resulting structure; (g) a working electrode 11 atop the porous membrane 16; (h) a second circuit connector 9' expanding to the working electrode 11; (i) upper substrate 10' covering with a second insulator 15' while exposing exception of the working electrode 11; (j) a plurality of differential circuit connectors 90 formed below the lower substrate 10; (k) a differential counter electrode 120 and a differential reference electrode 130; (l) a differential insulator 150 formed on the differential circuit connectors 90; (m) a differential porous membrane 160; (n) a differential adhesive 170 with the exception of the porous membrane 160; (o) a differential working electrode 110 atop the differential porous membrane 160; (p) a second differential circuit connector 90' with the differential adhesive 170; (q) a differential second insulator 150'; and (r) a differential upper substrate 100, each of the differential component, established on symmetry with respect to the lower substrate 10, which functions in the same pattern as that of its corresponding one in the opposite module.

In another embodiment of the present invention, it can be provided a differential face-to-face type biosensor with a two-electrode system, consisting of the counter electrode 12 on the first circuit connector 9 on the lower substrate 10 and the working electrode 11 formed on second circuit connector 9' on the upper substrate 10'. Except said the electrode system, it has the same structure as differential face-to-face type biosensor in the three-electrode system.

In the differential face-to-face type biosensor, glucose oxidase and an electron transfer mediator may be immobilized onto the porous membrane 16 while bovine serum albumin is fixed onto the differential porous membrane 160.

In accordance with a further embodiment of the present invention, there are provided a face-to-face and a flat type biosensors, comprising: (a) a lower substrate; (b) an electrode system patterned on the lower substrate; (c) an adhesive covered over the lower substrate the exception of porous membrane, serving as an insulator; (d) a porous membrane being intercalated between the counter electrode and the working electrode, fixed with an adhesive; (e) a electrode positioned facing on the porous membrane, and a hole of upper substrate; and (f) an upper substrate containing a sample inlet for protecting the porous membrane as well as being introducible samples to the biosensor.

With reference to FIG. 4, there is shown a face-to-face type biosensor adopting a three-electrode system.

Figure 4A:
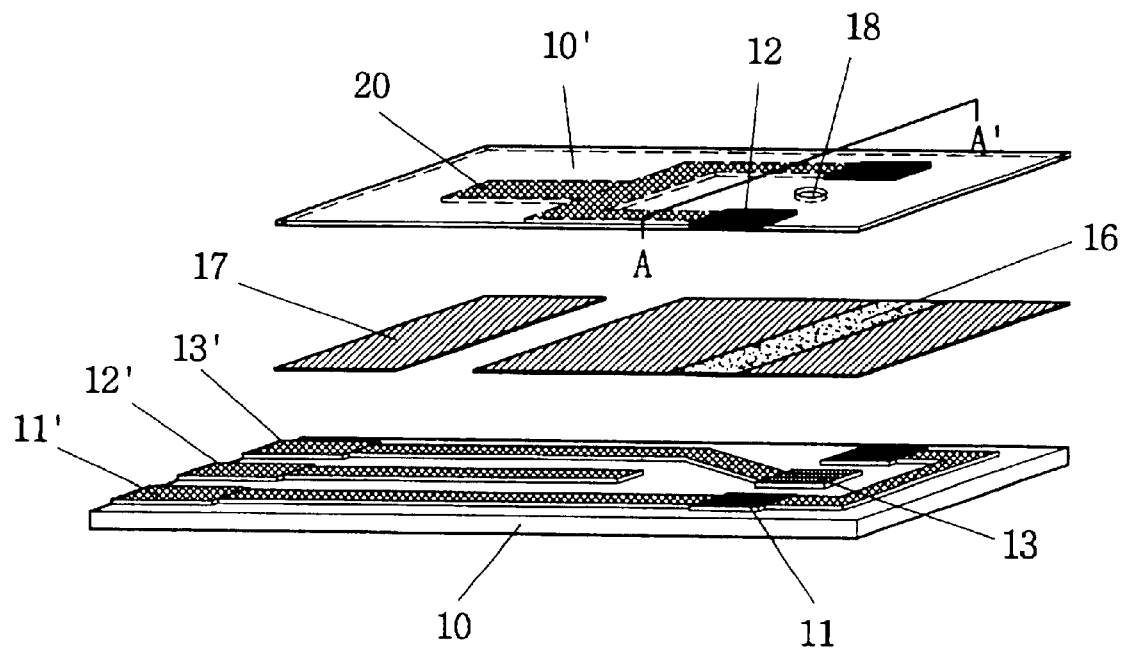
FIG. 4a is an exploded perspective view showing a face-to-face type biosensor adopting a three-electrode system, in accordance with a third embodiment of the present invention.

As seen in FIG. 4a, the face-to-face type biosensor comprises: (a) a lower substrate 10; (b) an electrode system formed on the lower substrate 10, consisting of a J-shaped working electrode connector strip 11' with a working electrode 11 established thereon, a counter electrode connector strip 12', and a reference electrode connector strip 13' with a reference electrode 13 established thereon; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, and (f) an upper substrate 10', fixed by the adhesive 17, having a hole of upper substrate 18 through which samples are introduced inside the biosensor.

The working electrode connector strip 11' is fabricated by printing silver ink, followed by printing carbon ink on the silver line to form the working electrode 11. Silver ink is printed to form the reference electrode connector strip 13' on which silver chloride is coated to form the reference electrode 13. Connected to the electrode connector strip 20, the counter electrode connector strip 12' is also printed with silver ink. As for the counter electrode 12, it is fabricated by printing carbon ink on branched line end areas of the Y-shaped electrode connector strip 20.

Figure 4B:
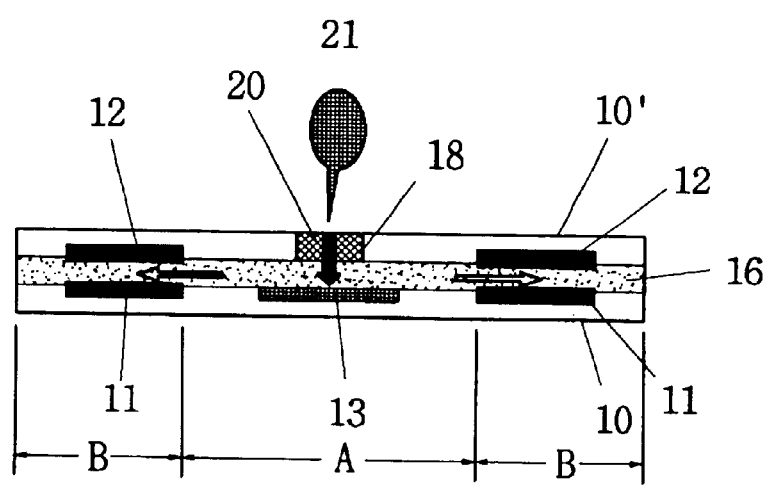
FIG. 4b is a cross sectional view, taken along the line A–A' of FIG. 4a, in which reference character "A" denotes a whole blood region and reference character "B" denotes separated plasma regions.

When a whole blood sample is introduced into the biosensor through the hole upper substrate 18 as shown in FIG. 4b, the porous membrane 16 intercalated between the upper substrate 10' and lower substrate 10 removes platelets and blood cells from the whole blood sample at the A region while blood plasma is separated at the B region to reach the working electrode 11 and the counter electrode 12, which face each other. This porous membrane built-in biosensor may comprise a sample inlet, so that the amount of samples absorbed to the porous membrane is constantly controlled. At the sample inlet, detection signals, which are amplified by 2 to 5 times can be provided by the symmetrically distributed electrode having a Y-shape.

Figure 5A:
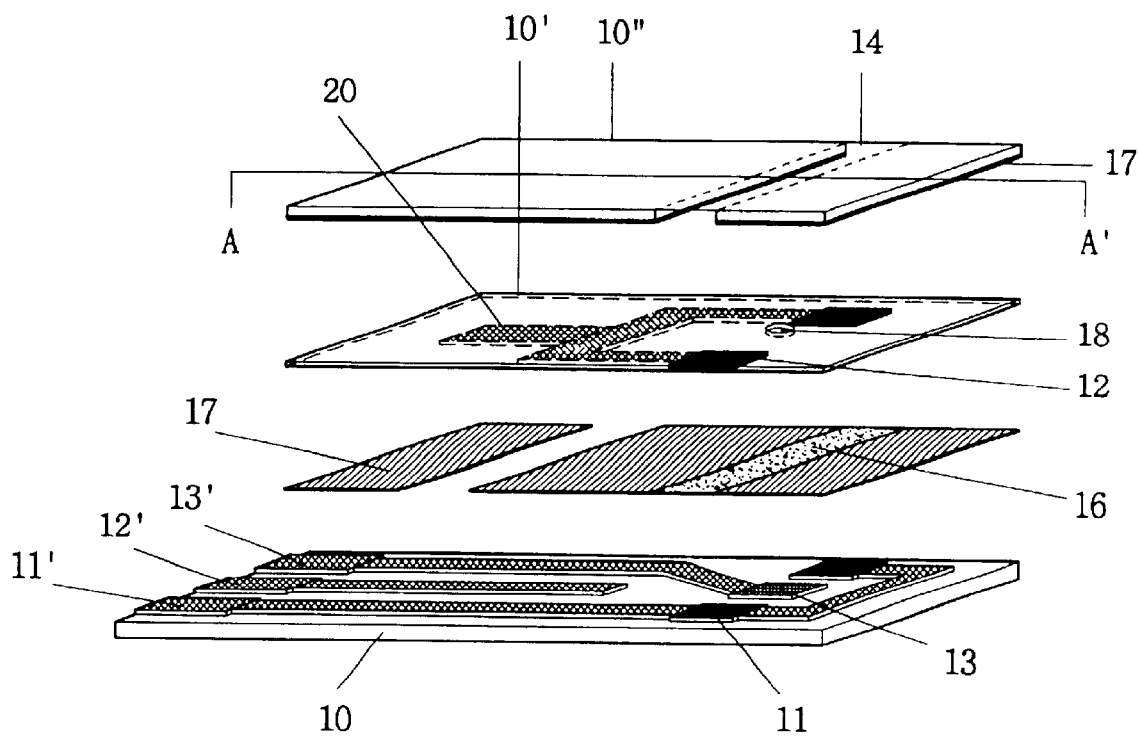
FIG. 5a is an exploded perspective view showing a face-to-face type biosensor adopting a three-electrode system and having a sample inlet which is formed traversing the electrode system, in accordance with a fourth embodiment of the present invention.
Figure 5B:
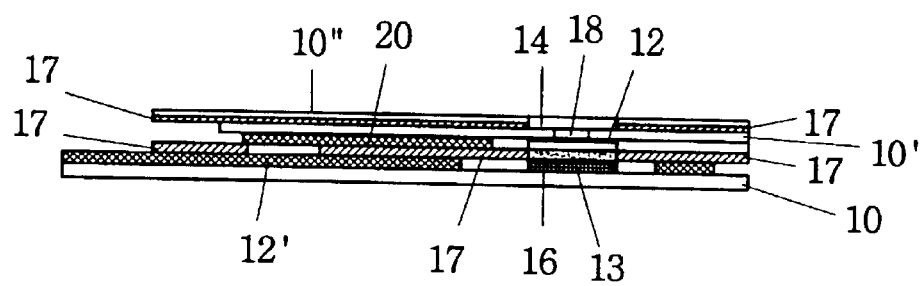

With reference to FIG. 5, there is shown as a face-to-face type biosensor with a three-electrode system, which has a sample inlet 14 formed in the transverse direction of the electrode.

As seen in FIG. 5a, the face-to-face type biosensor comprises: (a) a lower substrate 10; (b) an electrode system formed on the lower substrate 10, consisting of a J-shaped working electrode connector strip 11' with a working electrode 11 established thereon, a counter electrode connector strip 12', and a reference electrode connector strip 13' with a reference electrode 13 established thereon; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, and (f) an upper substrate 10', fixed by the adhesive 17, having a hole of upper substrate 18; and (g) a second upper substrate 10", fixed to the first upper substrate 10' via an adhesive 17, having a sample inlet 14, which is formed in the direction traversing the electrode system, wherein the sample inlet has two opposite open ends through which samples are introduced to the biosensor.

The working electrode connector strip 11' is fabricated by printing silver ink, followed by printing carbon ink on the silver line to form the working electrode 11. Silver ink is printed to form the reference electrode connector strip 13' on which silver chloride is coated to form the reference electrode 13. Connected to the electrode connector strip 20, the counter electrode connector strip 12' is also printed with silver ink. As for the counter electrode 12, it is fabricated by printing carbon ink on branched end areas of the Y-shaped electrode connector strip 20. The sample inlet 14 of the biosensor may be formed by pressing a second upper substrate 10" made of a plastic in a mold or coating, over the first upper substrate 10', an adhesive, such as double-sided adhesive tape, having an opening as wide as the porous membrane 16.

After being taken from the body using a lancet, a blood sample is brought into contact with one end of the sample inlet 14. This biosensor requires only 3 μl or less of the sample to fill the sample inlet 14. This sample is transferred into the porous membrane 16 through the hole of upper substrate 18.

Figure 6:
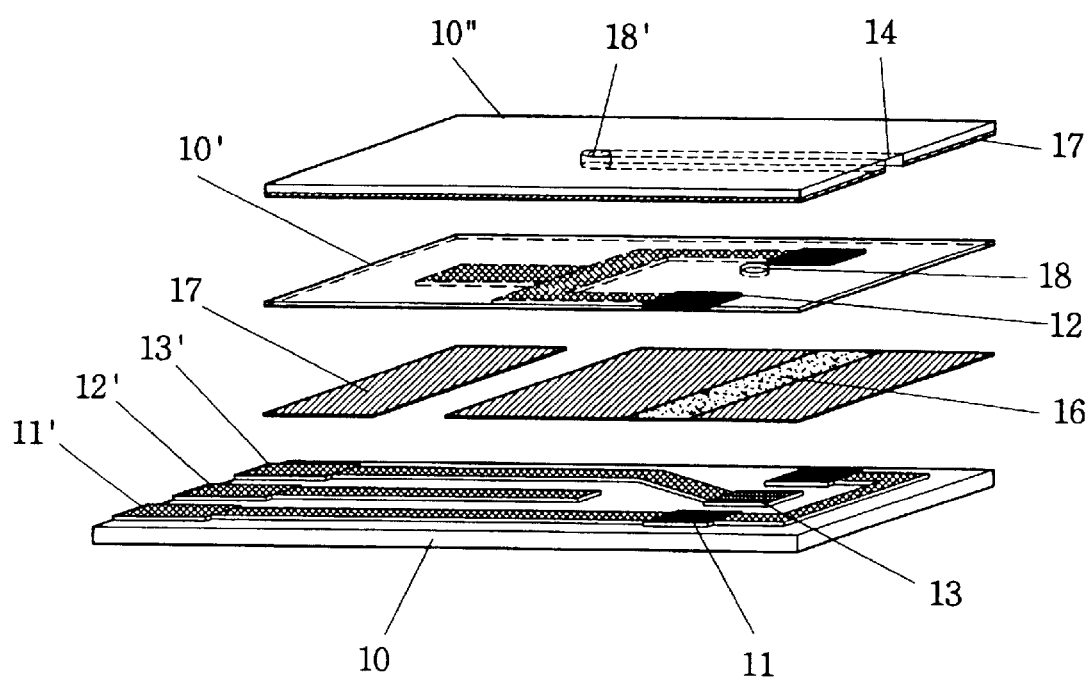
FIG. 6 is an exploded perspective view showing a face-to-face type biosensor adopting a three-electrode system and having a sample inlet which is formed in the same direction in the electrode system, in accordance with a fifth embodiment of the present invention.

With reference to FIG. 6, there is shown as a face-to-face type biosensor employing a three-electrode system, which has a sample inlet formed in the lengthwise direction of the electrode. As seen in FIG. 6, the face-to-face type biosensor comprises: (a) a lower substrate 10; (b) an electrode system formed on the lower substrate 10, consisting of a J-shaped working electrode connector strip 11' with a working electrode 11 established thereon, a counter electrode connector strip 12', and a reference electrode connector strip 13' with a reference electrode 13 established thereon; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, and (f) an upper substrate 10', via the adhesive 17, having a hole of upper substrate 18; and (g) a second upper substrate 10" with a second hole of upper substrate 18' fixed to the first upper substrate 10' via an adhesive 17, having a sample inlet 14 which is formed in the same direction as in the electrode system, extending from a mid point to an end of the second upper substrate 10", wherein the sample inlet has one open end through which samples are introduced to the biosensor.

Different from that of FIG. 5a in sample inlet shape, the biosensor of this embodiment has a sample inlet extending from one end of the second upper substrate 10" to a predetermined point. Also, this embodiment is characterized by the presence of the second hole of upper substrate 18' to make easy the introduction of samples from the sensor end.

Figure 7:
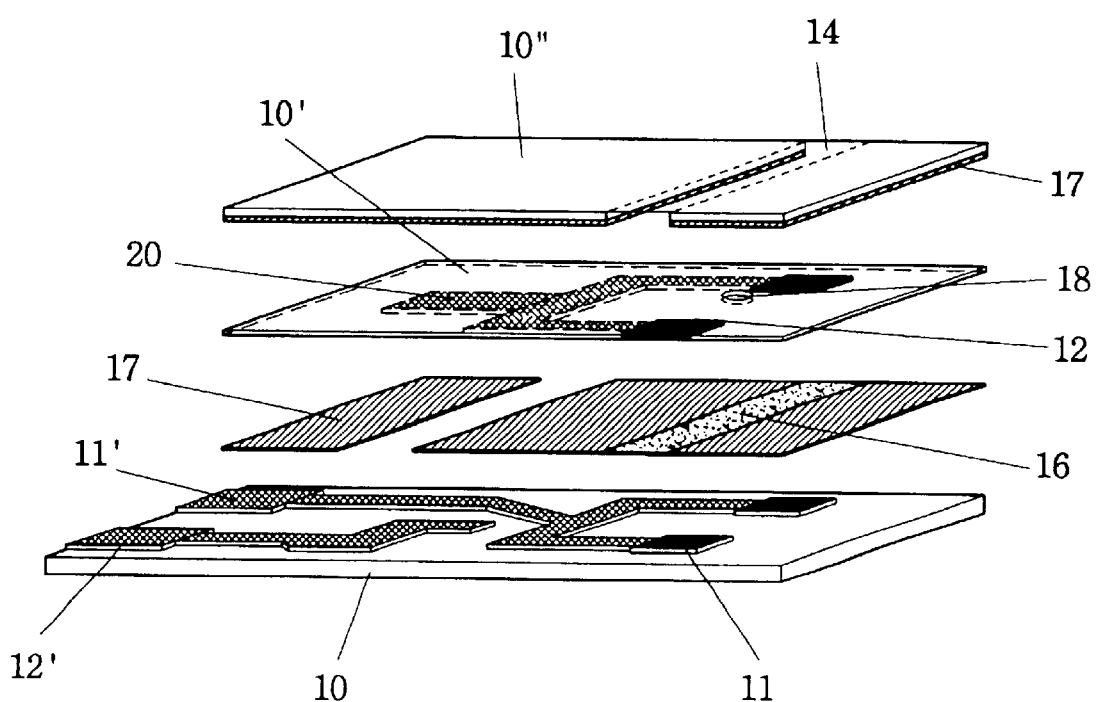
FIG. 7 is an exploded perspective view showing a face-to-face type biosensor adopting a two-electrode system and having a sample inlet, which is formed traversing the electrode system.

With reference to FIG. 7, there is shown as a face-to-face type biosensor employing a two-electrode system, which has a sample inlet formed in the transverse of the electrode. As seen in FIG. 7, the face-to-face type biosensor comprises: (a) a lower substrate 10; (b) an electrode system formed on the lower substrate 10, consisting of a Y-shaped working electrode connector strip 11' with a working electrode 11 established thereon and a counter electrode connector strip 12', the latter it is connected to one end portion of the circuit connector strip 20 on the upper substrate 10'; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, and (f) an upper substrate 10', via the adhesive 17, having a hole of upper substrate 18; and (g) a second upper substrate 10", having a sample inlet 14, fixed to the first upper substrate 10' via an adhesive 17, wherein said a sample inlet 14 is formed in the direction traversing the electrode system, wherein the sample inlet has two opposite open ends through which samples are introduced to the biosensor.

Figure 8A:
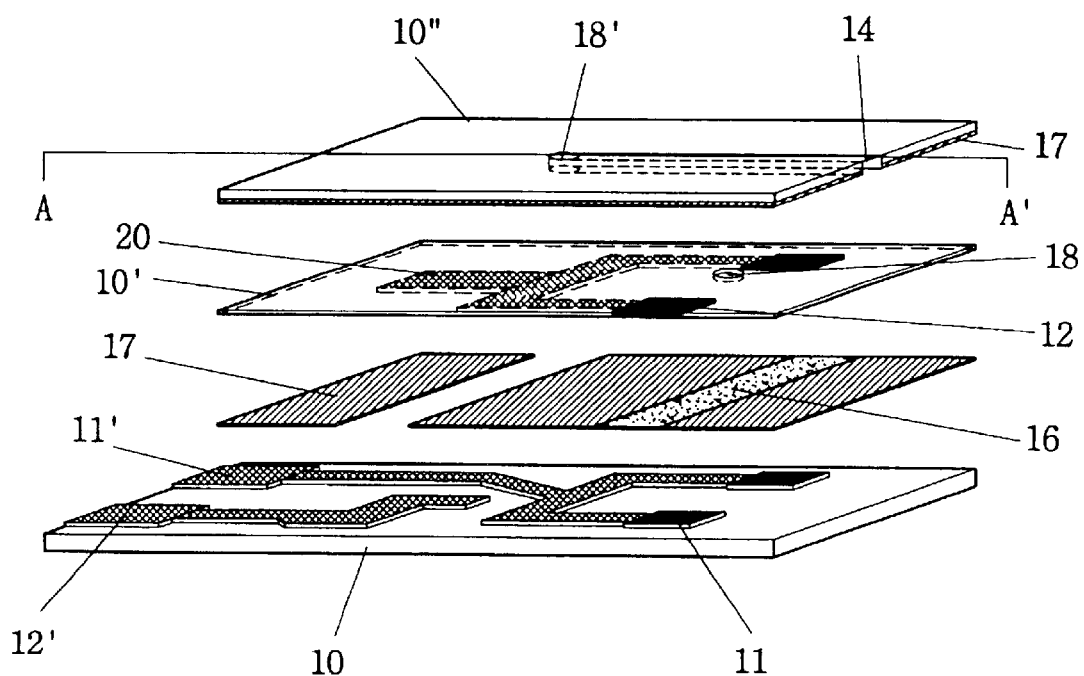
FIG. 8a is an exploded perspective view showing face-to-face type biosensor adopting a two-electrode system and having a sample inlet, which is formed in the same direction as in the electrode system.
Figure 8B:
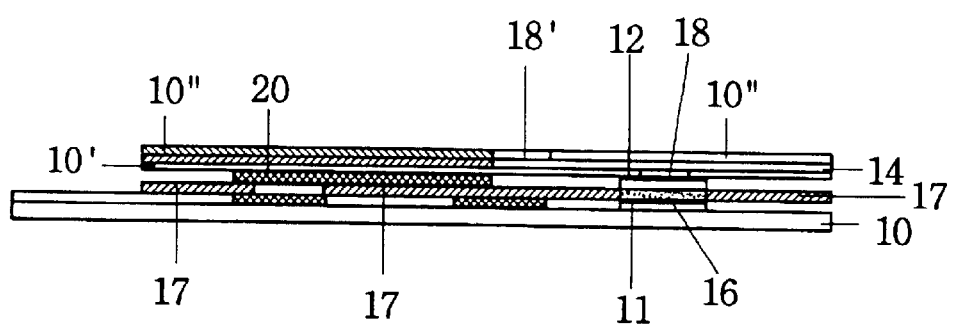

Like that of FIG. 7, the biosensor of FIG. 8 adopts a two-electrode system, which has a sample inlet 14 formed in the same direction of the electrode. As seen in FIG. 8, the face-to-face type biosensor comprises: (a) a lower substrate 10; (b) an electrode system formed on the lower substrate 10, consisting of a Y-shaped working electrode connector strip 11' with a working electrode 11 established thereon and a counter electrode connector strip 12' established thereon; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, (f) an upper substrate 10', fixed by the adhesive 17, having a hole of upper substrate 18; and (g) a second upper substrate 10" with a second hole of upper substrate 18', having a sample inlet 14, fixed to the first upper substrate 10' via an adhesive 17, wherein said a sample inlet 14 is formed in the same direction as in the electrode system, wherein the sample inlet has one open end through which samples are introduced to the biosensor.

The biosensor of FIG. 8 is a face-to-face type biosensor adopting a two-electrode system. A sample inlet 14, with an opening as wide as the porous membrane 16, may be fabricated from an adhesive 17 which is not applied to the second upper substrate 10". Samples can be introduced to the biosensor from the end thereof. After being introduced through the sample inlet 14, the sample is transferred to the porous membrane 16 through the hole upper substrate 18.

Figure 9:
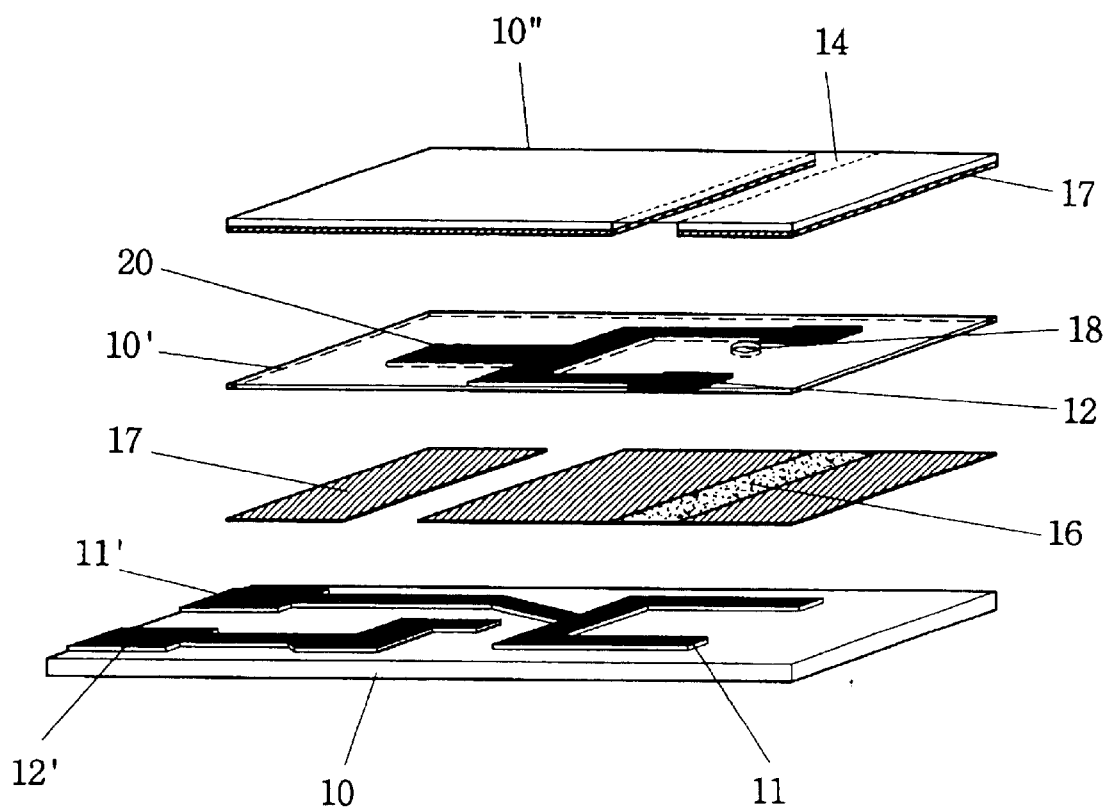
FIG. 9 is an exploded perspective view showing a face-to-face type biosensor adopting a two-electrode system made of carbon ink only and having a sample inlet, which is formed traversing the electrode system.

With reference to FIG. 9, there is shown a face-to-face type biosensor adopting a two-electrode system, in which a sample inlet extends in the transverse direction and the all electrode system is formed of only carbon ink. As seen in the exploded perspective view of FIG. 9, comprises: (a) a lower substrate 10; (b) an electrode system formed on the lower substrate 10, consisting of a Y-shaped working electrode connector strip 11' with a working electrode 11 established thereon and a counter electrode connector strip 12'; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, (f) an upper substrate 10', formed on the adhesive 17, having a hole of upper substrate 18; and (g) a second upper substrate 10", having a sample inlet 14, fixed to the first upper substrate 10' via an adhesive 17, wherein said a sample inlet 14 is formed in the direction traversing the electrode system, wherein the sample inlet has two opposite open ends through which samples are introduced to the biosensor.

An oxidase and an electron transfer mediator may be immobilized on the porous membrane 16 or the working electrode 11. In this structure, a sample can be introduced from both the left and right side ends of the biosensor.

As mentioned above, the working electrode connector strip 11' is fabricated from carbon ink by printing. Also, the counter electrode connector strip 12' to be connected to the electrode connector strip 20 is also printed with carbon ink. In addition to serving an adhesive 17 as an insulator, the intermediate membrane is formed in such a pattern that it has openings at one of which the porous membrane 16 is present and through one of which the counter electrode connector strip 12' is contacted with one end portion of the electrode connector strip 20. This biosensor is characterized in that all electrodes are made of carbon ink only, without using silver ink.

After being introduced to the biosensor through the hole upper substrate 18 of the first upper substrate 10', whole blood samples are transferred to the porous membrane 16 between the upper and the lower substrates and then move chromatographically. This porous membrane built-in biosensor may comprise a sample inlet 14, so that the amount of sample absorbed to the porous membrane is constantly controlled.

Figure 10A:
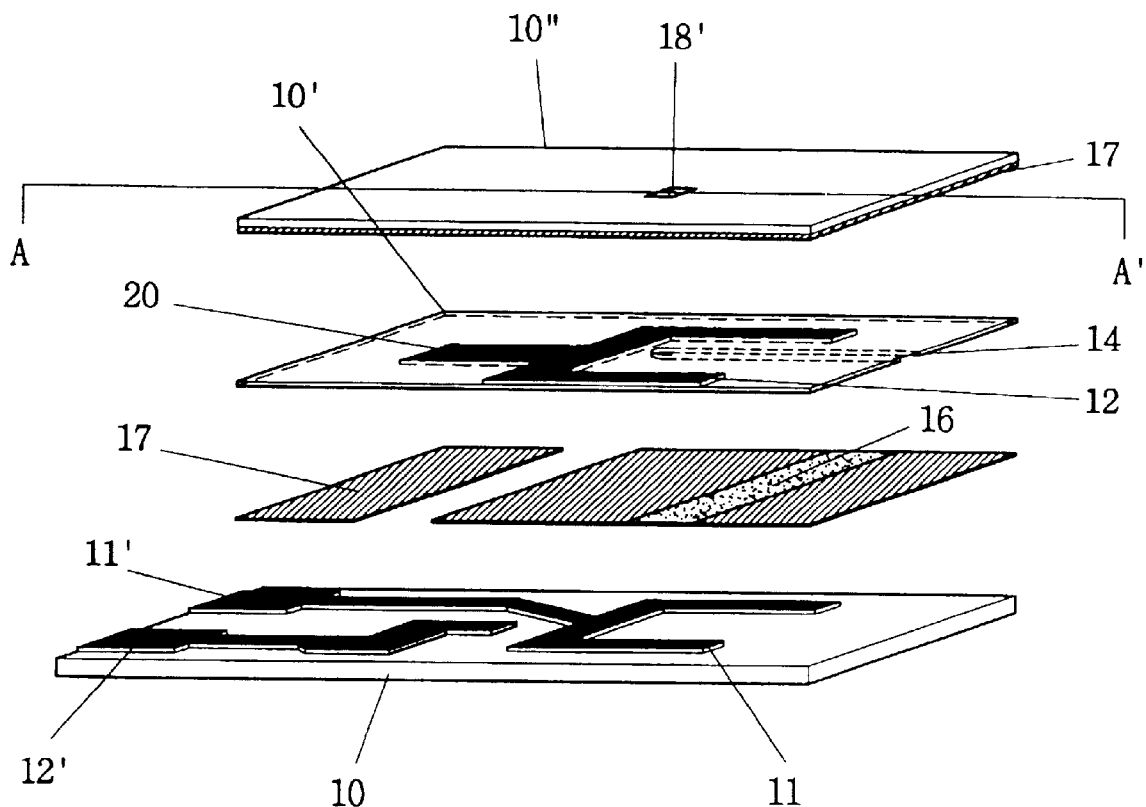
FIG. 10a is an exploded perspective view showing a face-to-face biosensor adopting a two-electrode system made of carbon ink only and having a sample inlet, which is formed in the same direction as in the electrode system.
Figure 10B:
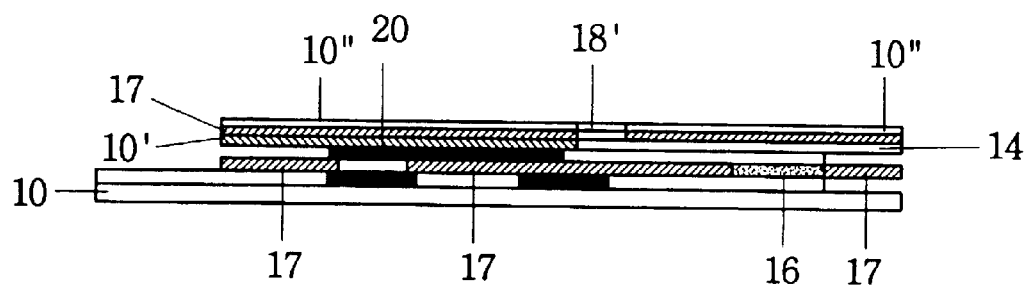

FIG. 10 illustrates a face-to-face type biosensor adopting a two-electrode system; characterized in that a sample inlet 14 is formed in an upper substrate 10' not in a second upper substrate 10" and all electrodes are fabricated by carbon ink. This face-to-face type biosensor comprises: (a) a lower substrate 10; (b) an electrode system formed on the lower substrate 10, consisting of a Y-shaped working electrode connector strip 11' with a working electrode 11 established thereon and a counter electrode connector strip 12', all of the electrodes coating carbon ink only; (c) a porous membrane 16, formed on a predetermined area of the electrode system, covering the working electrode 11; (d) an adhesive 17 covered over the lower substrate 10 with the exception of the porous membrane 16; (e) a Y-shaped circuit connector strip 20 with a counter electrode 12 coated with carbon ink only, (f) an upper substrate 10', fixed by the adhesive 17, having a sample inlet 14 extending in the lengthwise direction to one end of the upper substrate 10' from a mid point and thus having an open end; and (g) a second upper substrate 10", fixed to the first upper substrate 10' via an adhesive 17, having a second hole of upper substrate 18'.

All of the electrodes are made of carbon ink. An oxidase and an electron transfer mediator may be immobilized on the porous membrane 16 or the working electrode 11. In this structure, a sample can be introduced from the end of the sensors of the biosensor.

A sample inlet 14, with an opening as wide as the porous membrane 16, may be fabricated from an adhesive 17 which is not applied to the upper substrate 10'. The sample inlet 14 enables the introduction of samples at the end of the biosensor.

In addition, the present invention provides a biosensor with a modified sample inlet capable of rapidly introducing a predetermined amount of blood samples and increasing accuracy and reproducibility.

Figure 11:
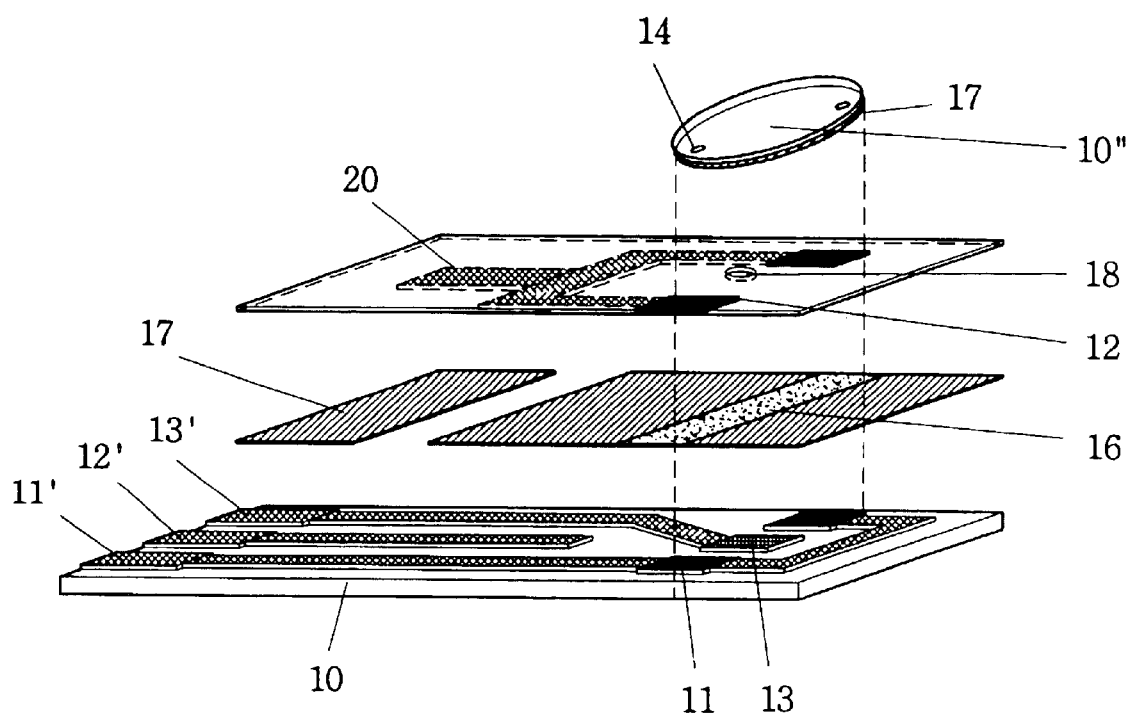
FIG. 11 is an exploded perspective view showing a face-to-face biosensor adopting a three-electrode system and having a modified sample inlet in which a circular space is provided.

With reference FIG. 11, there is shown a face-to-face biosensor adopting a three-electrode system, characterized by providing a circular space for a sample inlet. The biosensor comprises: (a) a lower substrate 10; (b) an electrode system formed on the lower substrate 10, consisting of a J-shaped working electrode connector strip 11' with a working electrode 11 established thereon, a counter electrode connector strip 12', and a reference electrode connector strip 13' with a reference electrode 13 established thereon; (c) a porous membrane 16, either said porous membrane 16 or the working electrode 11 having an oxidase and an electron transfer mediator immobilized thereto; (d) an adhesive 17 covered over the lower substrate 10 with the exception of the porous membrane 16; (e) a Y-shaped circuit connector strip 20 with a counter electrode 12 on the branched line ends, (f) an upper substrate 10', fixed by the adhesive 17, having a hole of upper substrate 18 through which samples are introduced inside the biosensor. (g) a circular second upper substrate 10" with a circular sample inlet 14, fixed to the first upper substrate 10' via an adhesive 17.

This biosensor may fabricated by fixing the circular second upper substrate 10" to the biosensor of FIG. 5a by use of the adhesive 17, said the second upper substrate 10" being provided with a modified sample inlet 14.

In another embodiment of the present invention, it can be provided a two-electrode system biosensor which has the same structure as in this biosensor, with exception that a counter electrode connector strip 12' and a J-shaped working electrode connector strip 11' with a working electrode 11 established on its branched end line area are formed on the lower substrate and a counter electrode 12 is formed on the upper substrate 10'.

Figure 12:
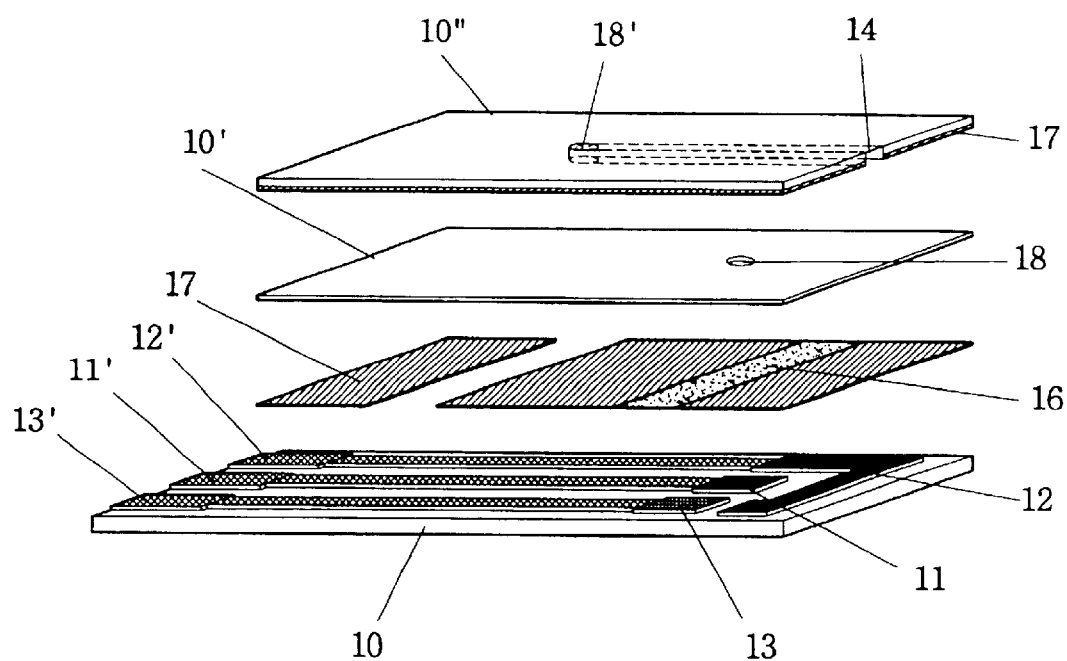
FIG. 12 is an exploded perspective view showing a flat type biosensor adopting a three-electrode system and having a sample inlet, which is formed in the same direction as in the electrode system.

With reference to FIG. 12, there is shown a flat type biosensor adopting a three-electrode system, characterized by the sample inlet, which is formed in the second upper substrate 10'", extending from a mid point to one end of the substrate. The biosensor comprises: (a) a lower substrate 10; (b) a electrode system, formed on the lower substrate 10, consisting of a working electrode connector strip 11' with a working electrode 11 established thereon, a counter electrode connector strip 12' with a J-shaped counter electrode 12 established thereon, and a reference electrode connector strip 13' with a reference electrode 13 established thereon; (c) a porous membrane 16, formed on a predetermined area of the electrode system, covering the working electrode 11, and an adhesive 17 deposited over the intermediate membrane with the exception of the porous membrane 16; (d) a upper substrate 10' with a hole upper substrate 18 fixed to the lower substrate 10 via the adhesive 17; and (e) a second upper substrate 10" with a second hole of upper substrate 18', having a sample inlet 14, fixed to the first upper substrate 10' via an adhesive 17, wherein said a sample inlet 14 is formed straightly extending from a mid point to one end of the second upper substrate 10" and is introduced samples to the biosensor.

In the biosensor, the working electrode connector strip 11', the counter electrode connector strip 12', and the reference electrode connector strip 13' are printed with silver ink while the working electrode 11 and the counter electrode 12 are fabricated from carbon ink by printing. On the same plane, the reference electrode 13 is fabricated from silver chloride.

In addition to serving as an insulator and an intermediate membrane, a sample inlet 14, with an opening as wide as the porous membrane 16, may be fabricated from an adhesive 17 which is not applied to the second upper substrate 10". The first upper substrate 10' is provided with the hole upper substrate 18 through which samples are introduced into the biosensor, being covered with a second upper substrate 10" having the sample inlet 14 which has one open end through which samples are introduced to the biosensor.

In another embodiment of the present invention, there is provided a flat type biosensor with two-electrode system, which has the same structure as in this biosensor, with exception that a counter electrode connector strip 12' with a counter electrode 12 established thereon and a working electrode connector strip 11' with a working electrode 11 established on thereon are formed on lower substrate 10.

Figure 13:
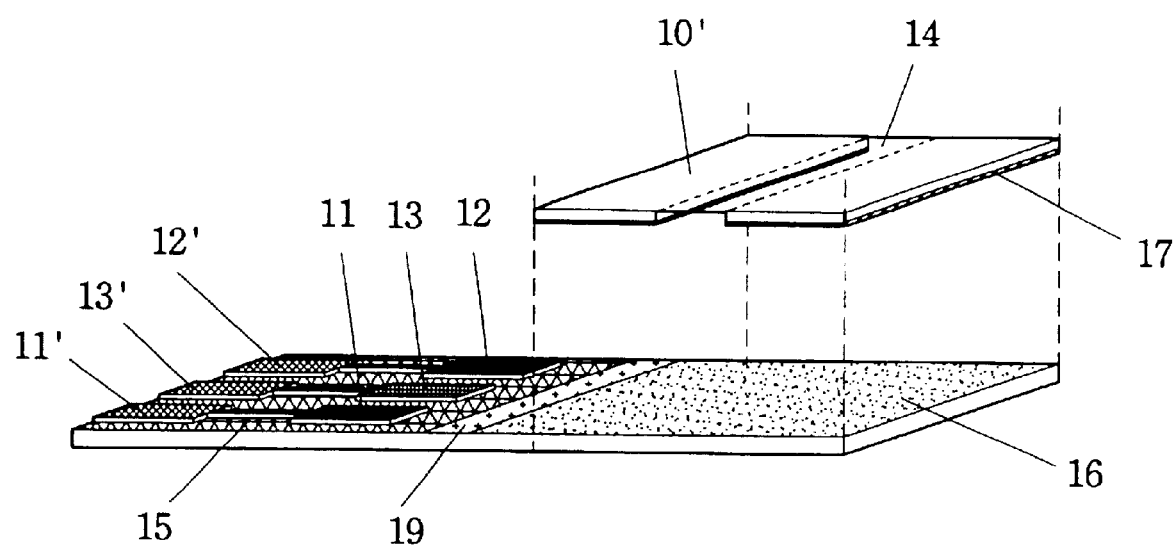
FIG. 13 is an exploded perspective view showing a flat type biosensor adopting a three-electrode system and having a porous membrane as a lower substrate, and a sample inlet, which is formed traversing the electrode system.

FIG. 13 shows a flat type biosensor which has a porous membrane as a substrate and a sample inlet running in the widthwise direction. As seen in the exploded perspective view of FIG. 13, the flat type biosensor comprises: (a) a lower substrate made of a porous membrane 16; (b) an insulator 15 formed on one half portion of the lower substrate 16, an electrode system, formed on the insulator 15, consisting of a working electrode connector strip 11' with a working electrode 11 established thereon, a counter electrode connector strip 12' with a counter electrode 12 established thereon, and a reference electrode connector strip 13' with a reference electrode 13 established thereon, and a pretreatment layer 19 adjacent to the insulator 15; and (c) an upper substrate 10' fixed onto the another half portion of the porous membrane 16 via an adhesive 17, having an sample inlet 14 which is formed in the direction traversing the electrode system and has two open ends. Through the sample inlet having two open ends, samples can be introduced from both the left and right ends of the biosensor adopting the three-electrode system.

As mentioned, a porous membrane 16 is used as a lower substrate. On one half portion of the porous membrane 16, an insulator is established to insulate samples and connector strips 11', 12' and 13' from one another. The working electrode 11 and the counter electrode 12 are formed of carbon ink by printing while the reference electrode is printed with silver chloride. In order to make the electrodes uniform in area and insulate the connector strips from one another, an insulator is printed again. A sample inlet 14 through which a predetermined amount of samples is introduced into the biosensor is provided to the upper substrate 10'. A blood sample is separated into its components by the porous membrane 16 before reaching the working electrode 11, so that only plasma components are detected. Functioning to oxidize interfering materials before a sample is introduced to the electrodes, the pretreatment layer ensures the accurate quantitative measurement of only a component of interest.

In accordance with another embodiment, there is provided flat type biosensor with a two-electrode system, which has the same structure as in this biosensor, with exception that only a counter electrode connector strip 12' with a counter electrode 12 established thereon and a working electrode connector strip 11' with a working electrode 11 established thereon are formed on the lower substrate 10.

Substrates for use in the biosensors described above may be formed of ceramic, plastics, silicon, alumina glass plates or polymeric materials with preference for an organic polymer selected from the group consisting of polyester, polyvinyl chloride, and polycarbonate.

For the fabrication of electrodes, such as reference electrodes, working electrodes and counter electrodes, silver, silver epoxy, palladium, copper, gold, platinum, silver/silver chloride, silver/silver ion, mercury/mercuric oxide, conductive carbon, and heavy metal oxides may be used. Preferably, a reference electrode material is selected form silver, silver epoxy, silver/silver chloride and silver/ silver ion, a working electrode material from conductive carbon, cobalt phthalocyanine paste, gold, platinum, and palladium, and a counter electrode material from conductive carbon, gold and platinum. These materials may be formed into reference, counter and working electrodes by a screen-printing method or a physical vapor deposition method. Preferred is a screen-printing method by virtue of its ability to treat various electrode materials with economical advantages, reproduce electrodes with consistency and make highly sensitive electrodes. In the screen-printing method, constant force is applied to a squeegee against open patterns to print ink or paste on predetermined areas of a substrate, thereby enabling the introduction of patterns in sequence. Another advantage with the screen-printing method is to activate the printed electrodes.

The dielectric layer 15 may be formed by screen-printing insulating polymer pastes followed by thermal treatment. Covered with the dielectric layers, the electrodes are maintained constant in their areas and thus improved in analytical reproducibility.

As for the protective membrane 22, it functions to physically protect porous membrane 16 immobilized to the oxidase and electron transfer mediator and is prepared from an organic polymer of good process ability, such as polyester, polyvinyl chloride or polycarbonate.

As an adhesive 17 suitable to firmly fix the porous membrane 16 and the protective membrane 22 to the electrode body, a double-sided adhesive tape or a conventional strong adhesive may be used. Preferred is a double-sided adhesive tape, which is as thick as the porous membrane. Said an adhesive 17 include to intermediate membrane, which has a gap at one of which the porous membrane 16 is present and through one of which the counter electrode connector strip 12' is contacted with one end portion of the electrode connector strip 20.

Characterized by numerous pores of 5 to 20 $\mu$m, the porous membrane 16 is formed of a paper, a hydrophilic organic polymer or a hygroscopic ceramic polymer, which is selected from the group consisting of nylon, hydrophilic polyester sulfone membranes, hydrophilic mixed cellulose esters, polytetrafluoroethylene membranes, polyvinylidine fluoride membranes, ion-selective membranes, glass fiber, polyester fiber or its modified fiber membranes. More Preferably, nitrocellulose paper, polyester fiber or its modified fiber membranes or similar filter paper may be used for the porous membrane.

Requirements for the electron transfer mediators immobilized to the porous membrane are that (1) their oxidized-reduced states in aqueous solution should be stable and reversible; (2) reduced electron transfer mediators should be non-reactive to oxygen; (3) their formal potentials should be low enough to exclude the influence of interfering materials to as large an extent as possible because their working potentials are determined by the formal potentials; (4) reduced electron transfer mediators should be oxidized relatively irrespective of pH; and (5) they should be non-reactive to electrochemically interfering materials, such as ascorbic acid, acetaminophene and uric acid. Concrete examples of the electron transfer mediators satisfying the requirements include hexaamineruthenium (III) chloride, potassium ferricyanide, potassium ferrocyanide, dimethyl-ferrocene (DMF), ferricinium, ferocene-monocarboxylic acid (FCOOH), 7,7,8,8-tetracyanoquinodimethane (TCNQ), tetrathiafulvalene (TTF), nickelocene (Nc), N-methyl acidinium ($NMA^+$), tetrathiatetracene (TTT), N-methylphenazinium ($NMP^+$), hydroquinone, 3-dimethylaminobenzoic acid (MBTHDMAB), 3-methyl-2-benzothiozolinone hydrazone, 2-methoxy-4-allylphenol, 4-aminoantipyrine (AAP), dimethylaniline, 4-aminoantipyrene, 4-methoxynaphthol, 3,3',5,5'-tetramethyl benzidine (TMB), 2,2-azino-di[3-ethyl-benzothiazoline sulfonate], o-dianisidine, o-toluidine, 2,4-dichlorophenol, 4-aminophenazone, benzidine and prussian blue as mixed-valence compounds capable of forming redox couples. Among them, hexaamineruthenium (III) chloride is the most preferable electron transfer mediator.

Examples of materials for use in fabrication of the sample inlet 14 include polyester and polyvinyl chloride with preference for polyester.

In the fabrication of a glucose sensor, surfactant is used to move samples quickly. Useful are non-ionic surfactants such as polyethylene glycol, oxyethylated alkylphenols (neonols), Triton X-100 and polyoxyethylated compounds; anionic surfactants such as sodium decyl sulfate; and cationic surfactants such as decylpuridium chloride, tetradecypyridium and pyridium. Triton X-100 is commercially used. Exemplified by CMC (carboxymethylcellulose), PVP (polyvinylpyrrolidone) and PVA (polyvinylalcohol), a dispersant is employed to disperse the oxidase and electron transfer mediator.

Herein, it should be understood that the present invention, although described for biosensors for analysis of blood glucose levels, can introduce appropriate enzymes and electron transfer mediator to the porous membrane so that a variety of samples, including bio-materials, such as metabolites, e.g., cholesterol, lactate, creatinine, proteins, hydrogen peroxide, alcohols, amino acids, and enzymes, e.g., GPT (glutamate pyruvate transaminase) and GOT (glutamate oxaloacetate transaminase), environmental materials, agricultural and industrial materials, and food materials can be quantitatively analyzed.

A better understanding of the present invention may be obtained in light of the following examples which are set forth to illustrate, but are not to be construed to limit the present invention.

EXAMPLE 1

Fabrication of Differential Flat Type Glucose Sensor

Step 1: Fabrication of Single Body

Silver/silver chloride paste was screen-printed on a polyester substrate 10 to give circuit connectors 9 and a reference electrode 13. Afterwards, a working electrode 11 and a counter electrode 12 were formed from conductive carbon paste through a screen-printing method, followed by the formation of a dielectric layer 15 from insulator paste (brand name: LS-405). Thermal treatment at 140° C. for 5 min yielded a single electrode body for a flat type biosensor.

Step 2: Fabrication of Flat Type Glucose Sensor

A porous nitrocellulose membrane (2×10 mm) was treated with MeOH for 30 min, washed with deionized water, and dried for about 1 hour. The porous nitrocellulose membrane or polyester fiber or its modified fiber membrane thus activated was soaked in a solution containing 100 mM hexaamineruthenium (III) chloride, a 0.5% (w/w) dispersant (carboxymethylcellulose), a 0.2% (w/w) surfactant (Triton X-100) and 10 mg/ml glucose oxidase for 1~2 hours with the aim of adsorbing the compounds thereto, and then allowed to stand for 16 hours at 24~26° C. at a humidity of 50~55% in a desiccator.

The resulting porous membrane was overlaid on the area-on-electrode of the flat type single electrode body prepared in step 1., and covered with a protective membrane 22 of polyester. Via a double-sided adhesive tape, the protective membrane was attached to the dielectric layer on the single electrode body to fabricate a flat type glucose sensor.

Step 3: Fabrication of Differential Flat Type Glucose Sensor

Figure 2A:
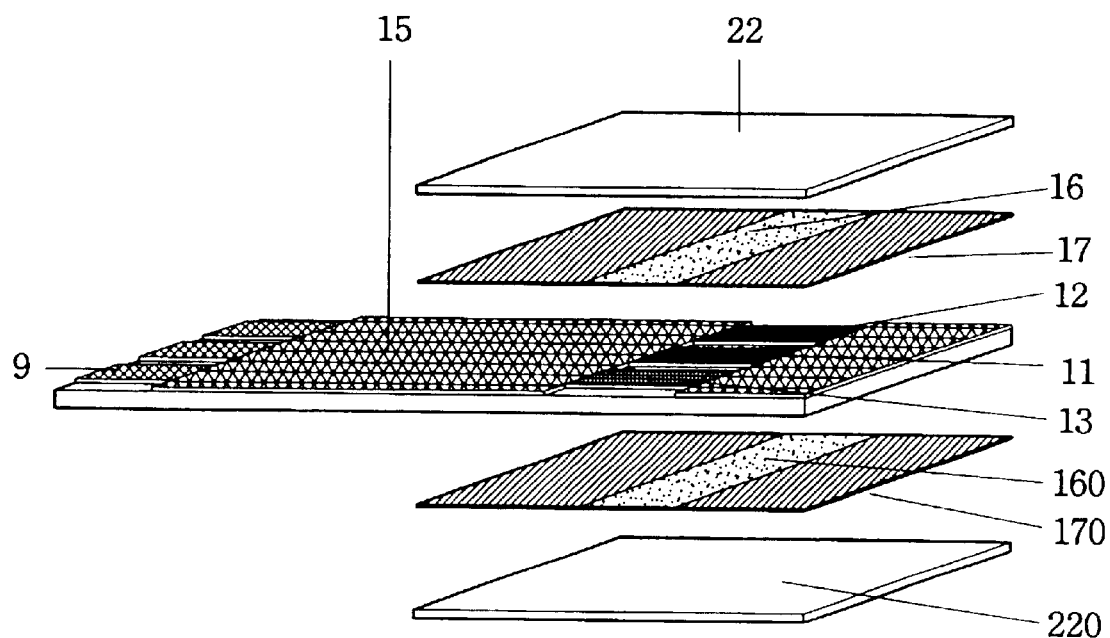
FIG. 2a is an exploded perspective view showing a differential flat type biosensor adopting a three-electrode system, in accordance with a first embodiment of the present invention.
Figure 2B:
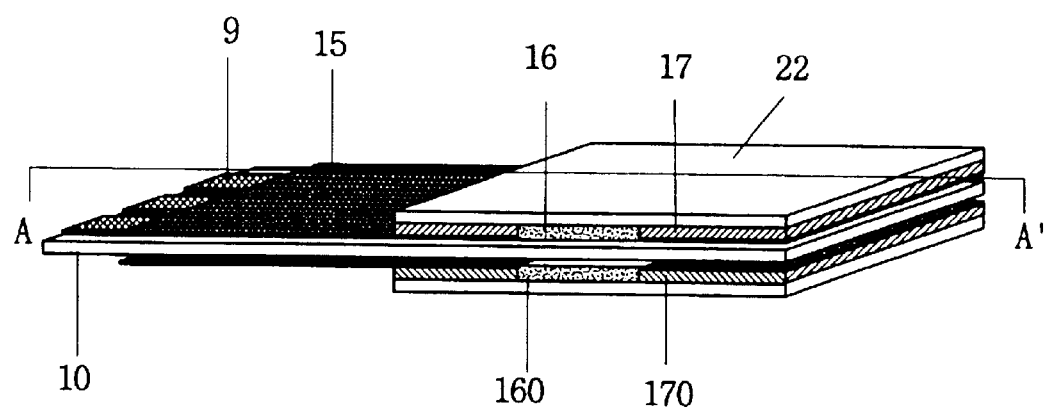
Figure 2C:
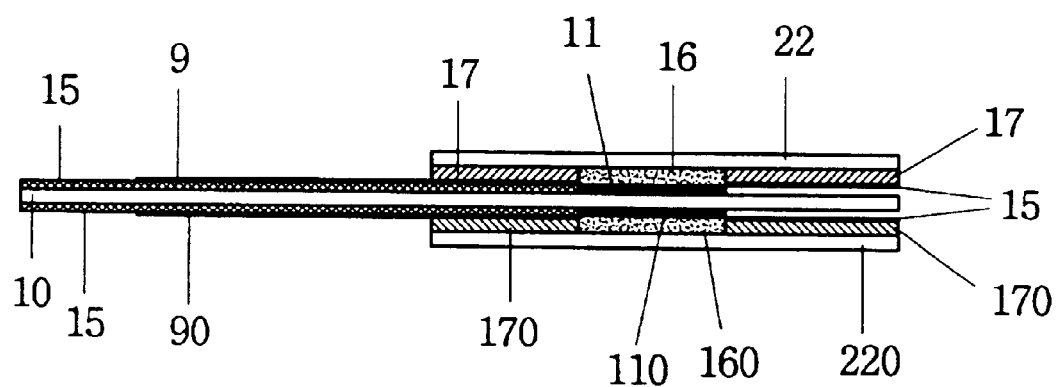
FIG. 2c is a cross sectional view, taken along line A–A' of FIG. 2b.

A flat type glucose sensor equipped prepared in step 2 of Example 1 contained a porous membrane 16 to which 100 mM potassium ferricyanide and glucose oxidase were immobilized. There was established on the backing surface of the lower substrate 10 a structure similar to that of the flat type glucose sensor, except that a differential porous membrane 160 to which 100 mM potassium ferricyanide and 10 mg/mL BSA (bovine serum albumin) were immobilized was provided, as shown in FIGS. 2a to 2c.

EXAMPLE 2

Fabrication of Differential Face-to-Face Type Glucose Sensor

Step 1: Fabrication of Double Electrode Body

As shown in FIGS. 3a to 3d, all components of the first electrode module, except for the working electrode, were formed in the same manner as in the single electrode body of the flat type glucose sensor. As for the second electrode module, its fabrication was as follows. On a polyester upper substrate 10', silver/silver chloride paste was screen-printed in the lengthwise direction to form second circuit connectors 9' on one end of which a working electrode 11 was formed from conductive carbon paste through a screen-printing method.

Step 2: Fabrication of Face-to-Face Type Glucose Sensor

A porous membrane 16 to which hexaamineruthenium (III) chloride and glucose oxidase were immobilized was prepared in the same manner as in step 2 of Example 1.

The porous membrane was placed on the counter electrode 12 and reference electrode 13 of the first electrode module, after the second electrode module was superimposed over the first electrode module in such a way that the working electrode 11 of the second electrode module faced the porous membrane 16. With the aid of a double-sided adhesive tape 17, the second electrode module was attached to the dielectric layer 15 on the first electrode module.

Step 3: Fabrication of Differential Face-to-Face Type Glucose Sensor

A face-to-face type glucose sensor equipped with a porous membrane 16 to which 100 mM potassium ferricyanide and glucose oxidase were immobilized was prepared in the same manner as in step 2 of Example 1. There was established on the backing surface of the lower substrate 10 a structure similar to that of the face-to-face type glucose sensor, except that a differential porous membrane 160 to which 100 mM potassium ferricyanide and 10 mg/mL BSA were immobilized was provided, as shown in FIGS. 3a to 3d.

EXAMPLE 3

Fabrication of Face-to-Face Type Glucose Sensor Equipped with Sample Inlet

Step 1 Fabrication of Double Electrode Body Equipped with Sample Inlet

On a lower substrate 10 of polyester, silver paste was printed to form the working electrode connector strip 11', the counter electrode connector strip 12' and the reference electrode strip 13'. A working electrode 11 and a reference electrode 13 were fabricated from conducting carbon paste and silver paste, respectively, to form a first electrode module. Separately, an electrode connector strip 20 was fabricated by silver paste and a counter electrode 12 was prepared by conducting carbon paste respectively, to form a second electrode module. In the second electrode module, a hole with a dimension of 1×2 mm was provided for use as a passage for sample.

Step 2 Fabrication of Face-to-Face Type Glucose Sensor Equipped with Sample Inlet After being subjected to physical absorption treatment, the porous membrane 16 fabricated in Step 2 of Example 1 was overlaid on the first electrode module. Over the first electrode module, the second electrode module was superposed to overlap the working electrode of the second electrode module with the porous membrane 16 and then, attached to the insulator 15 of the first electrode module via an adhesive 17 by compression. An adhesive 17 was applied onto the second electrode module with a sample inlet, followed by bonding a upper substrate with a sample to the adhesive to give a glucose sensor (FIGS. 4a and 4b).

In the following experimental examples, the biosensors of the present invention were characterized.

Experimental Example 1

Assay for Sample Amount to Be Introduced to Glucose Sensor Equipped with Sample Inlet To quantify the blood sample, which was introduced to each sensor of the glucose sensors equipped with a sample inlet, fabricated in Example 3, experiments were made.

Figure 14:
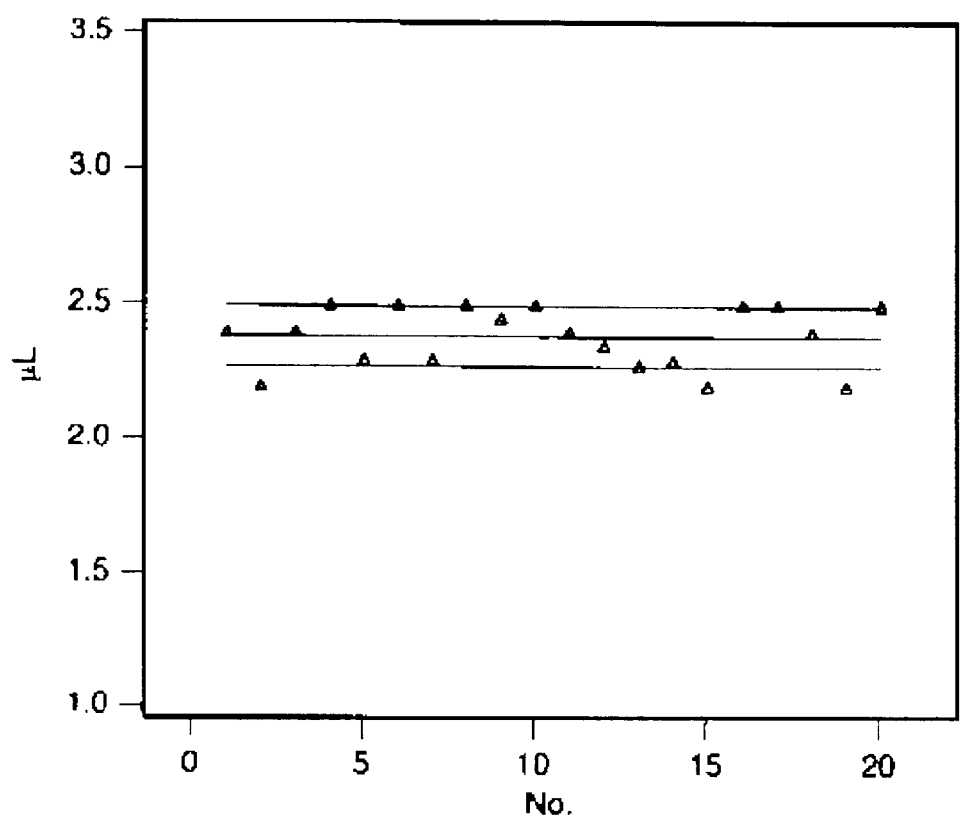
FIG. 14 is a graph in which the amounts of a sample introduced to a biosensor of the present invention are plotted with regard to numbers of test rounds.

As seen in FIG. 14, the sample amount introduced to the sensor was measured to be 2.38 μL on average as a result of using 20 sensors in total, with a standard deviation of ±0.11 μL, which demonstrated that the sample was introduced with very high accuracy.

Experimental Example 2

Influence of Interfering Materials on Flat Type Glucose Sensor

Figure 15:
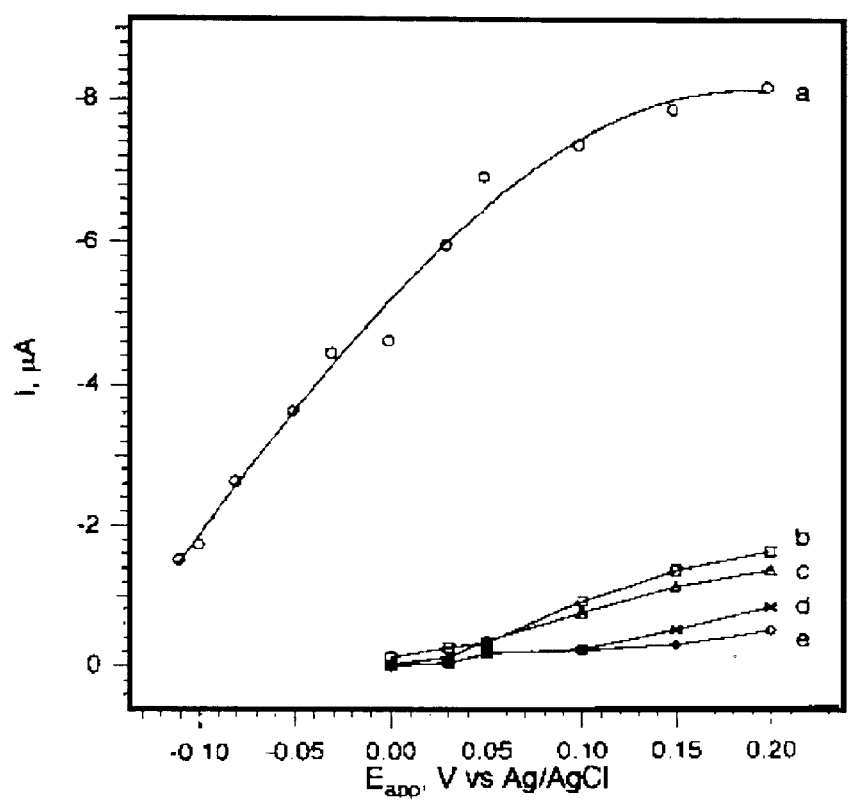
FIG. 15 is a graph showing the influence of interfering material on a flat type biosensor adopting a three-electrode system.

Dynamic curves, which show the influence of interfering materials such as ascorbic acid, acetaminophene and uric acid and a buffer solution, are depicted in FIG. 15. To obtain the dynamic curves, the flat type glucose sensor fabricated in Example 1 was measured for current change when the application potential versus the potential of a reference electrode (Ag/AgCl) was increased in the presence of 200 mg/dL glucose (11.1 mM) (a), 570 μM ascorbic acid (b), 660 μM acetaminophene (c), 916 μM uric acid (d) and a buffer solution (140 mM NaCl, PBS, pH 7.4) (e). As seen in FIG. 15, the sensor is affected only insignificantly at an application potential versus the reference electrode (Ag/AgCl) by the interfering materials.

Experimental Example 3

Influence of Blood Proteins on Flat Type Glucose Sensor

Figure 16:
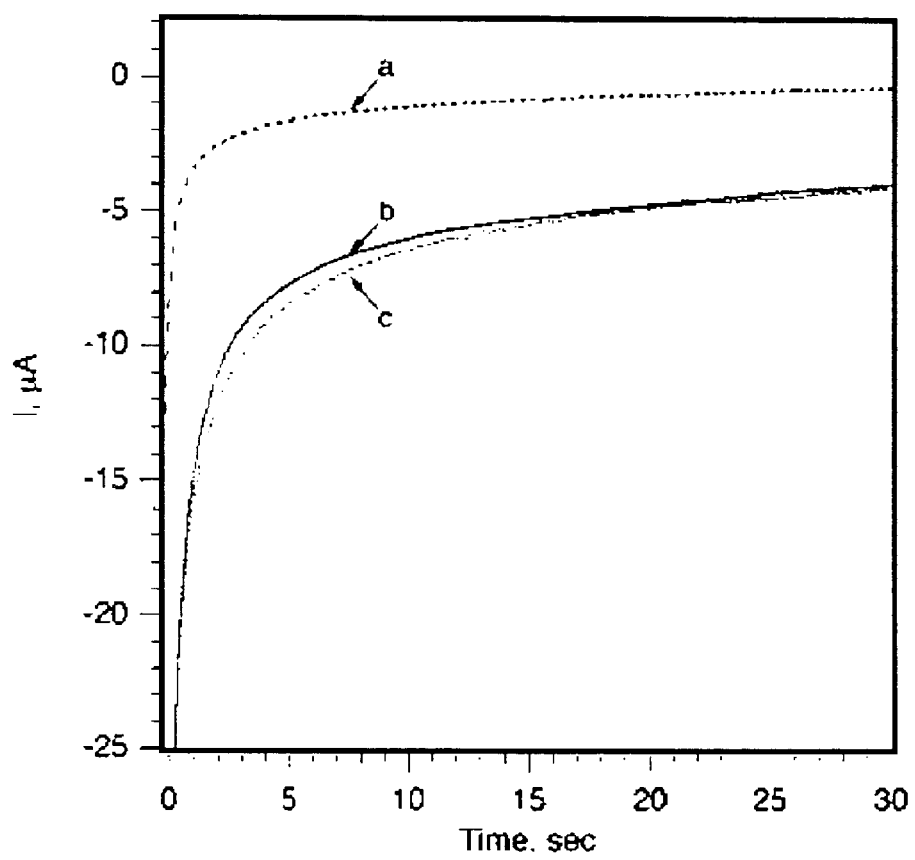
FIG. 16 shows chronoamperometric curves, illustrating the influence of blood hematocrit on the flat type biosensor of the invention.

Chronoamperometric curves, which show the influence of blood hematocrit on the flat type glucose sensor in step 2 of Example 1, are depicted in FIG. 16. To obtain these curves, the flat type glucose sensor was measured for current change at an application potential of 0.35 V vs. reference electrode in a buffer solution (140 mM NaCl, PBS pH 7.4) (a), whole blood (b), and plasma (c). The curve (b) for whole blood that contains blood hematocrits is almost identical to the curve (c) for plasma, which is deprived of blood hematocrits. The reason is that blood hematocrits are removed, in advance, in the glucose sensor because they cannot pass through pores of the sensor during the chromatographic motion of samples. Accordingly, the biosensor of the present invention was found to surmount the problem of conventional biosensors, in which detection reliability is poor because of the disturbance resulting from the adsorption of blood hematocrits to electrode surfaces.

Experimental Example 4

Figure 17:
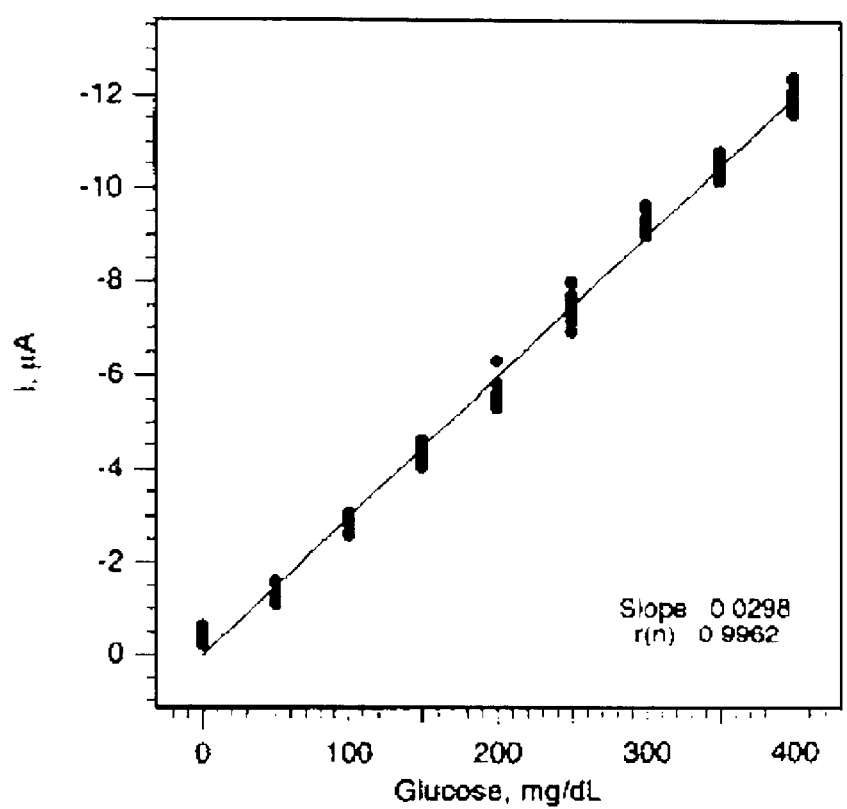
FIG. 17 is a calibration curve of a flat type glucose sensor for sensitivity to glucose standard solution adopting a three-electrode system.

Calibration Curve of Flat Type Glucose Sensor for Sensitivity to Glucose Standard Solution The flat type glucose sensor prepared in step 2 of Example 1 was assayed for sensitivity in glucose standard solutions with glucose concentrations of 0, 50, 100, 150, 200, 250, 300, 350 and 400 mg/dL. In this regard, current values were measured 10 times at each concentration under the electrical field of an application potential of 0.0 V vs. reference electrode. The calibration curve thus obtained is depicted in FIG. 17. Demonstrating that the flat type glucose sensor of the present invention is reliable, the curve was calculated to have a slope of 0.0298 [μA/(mg/dL)] and a linearity of as high as 0.996.

Experimental Example 5

Figure 18:
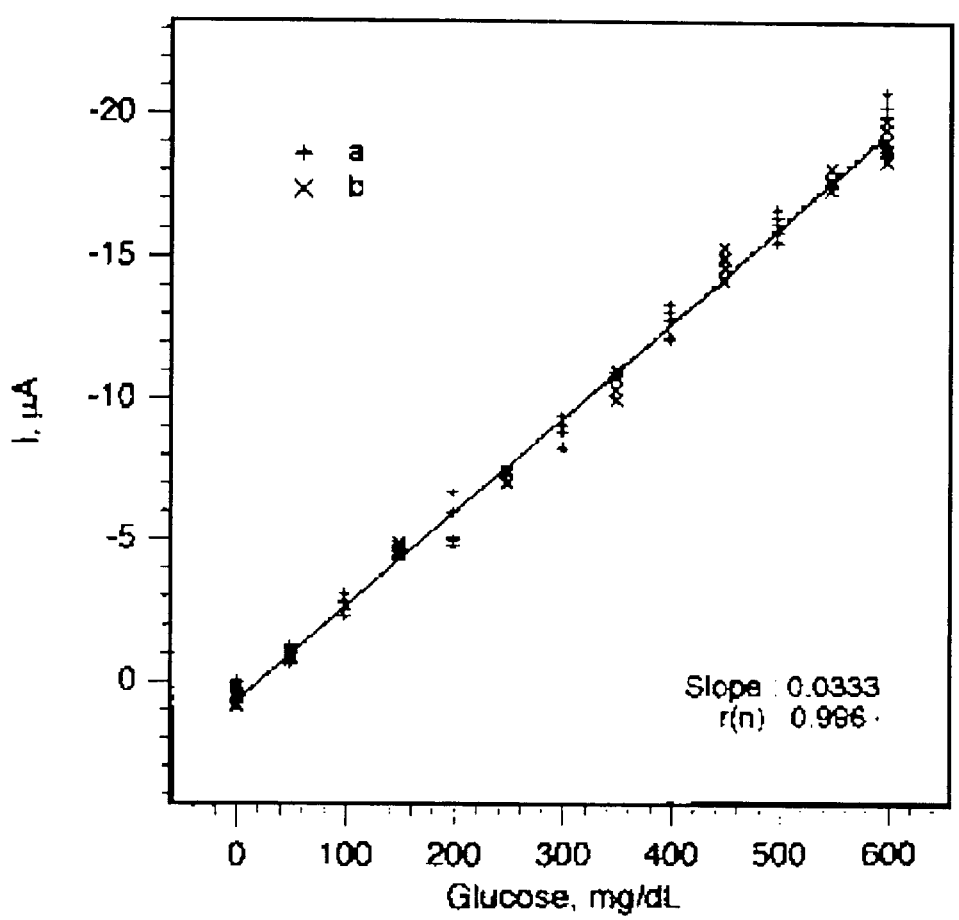
FIG. 18 is an calibration curve of a differential flat type glucose sensor for sensitivity to glucose standard solution adopting a three-electrode system.

Calibration Curve of Differential Flat Type Glucose Sensor for Sensitivity to Glucose Standard Solution The differential flat type glucose sensor prepared in Example 1 was assayed for sensitivity in glucose standard solutions with glucose concentrations of 0, 50, 100, 150, 200, 250, 300, 350 and 400 mg/dL. In this regard, current values were measured 5 times at each concentration under the electrical field of an application potential of 0.35 V vs. reference electrode in the presence of an interfering material (1 mM acetaminophene, 1 mM ascorbic acid, or 0.8 mM uric acid). The calibration curve thus obtained is depicted in FIG. 18. Demonstrating that the glucose sensor of the present invention is reliable, the curve was calculated to have a slope of 0.0333 [μA/(mg/dL)] and a linearity of as high as 0.996 irrespective of the interfering materials.

Using the differential flat type glucose sensor prepared in Example 1, normal serum and abnormal serum were measured 20 times for glucose level, each. The results are given in Table 1, below.

TABLE 1

|  | Normal serum | Abnormal serum |
| --- | --- | --- |
| Average, mg/dL | 91.6 | 298.5 |
| 2 SD, mg/dL | 9.4 | 30.9 |
| Coefficient of variation, % | 5.1 | 5.2 |
| Reference value, mg/dL | 91.9 ± 8.3 | 304.5 ± 31.0 |

As apparent from the data of Table 1, the differential flat type glucose sensor of the present invention was found to be accurate and precise as coefficients of variation was measured to be 5.1% and 5.2% for the normal serum and the abnormal serum, respectively.

Experimental Example 6

Figure 19:
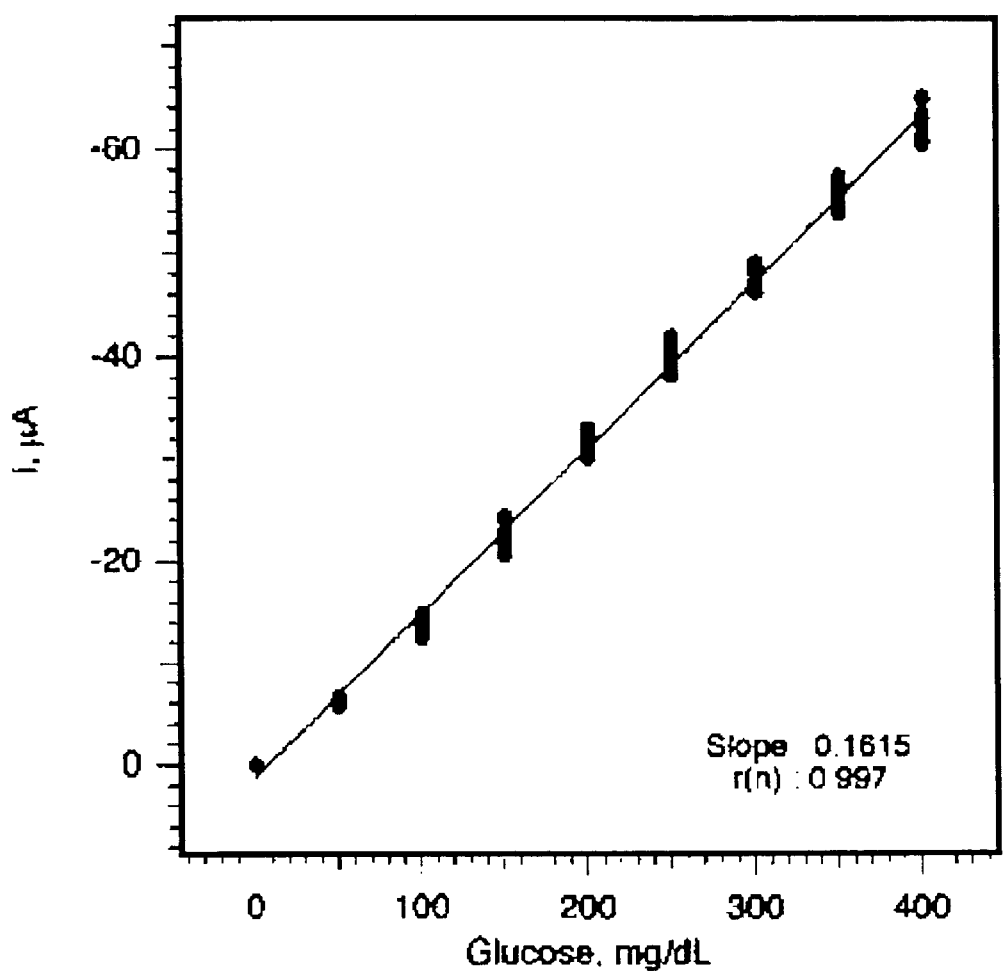
FIG. 19 shows an calibration curve of a face-to-face type glucose sensor for sensitivity to glucose standard solution adopting a three-electrode system.

Calibration Curve of Face-to-Face Type Glucose Sensor for Sensitivity to Glucose Standard Solution The face-to-face type glucose sensor prepared in step 2 of Example 2 was assayed for sensitivity in glucose standard solutions with glucose concentrations of 0, 50, 100, 150, 200, 250, 300, 350 and 400 mg/dL. In this regard, current values were measured 10 times at each concentration under the electrical field of an application potential of 0.0 V vs. reference electrode. The calibration curve thus obtained is depicted in FIG. 19. Demonstrating that the glucose sensor of the present invention is reliable, the curve was calculated to have a slope of 0.1615 [μA/(mg/dL)] and a linearity of as high as 0.997.

Using the face-to-face type glucose sensor prepared in step 2 of Example 2, normal serum and abnormal serum were measured 30 times for glucose level, each. The results are given in Table 2, below.

TABLE 2

|  | Normal serum | Abnormal serum |
| --- | --- | --- |
| Average, mg/dL | 91.4 | 291.9 |
| 2 SD, mg/dL | 5.0 | 11.8 |
| Coefficient of variation, % | 5.5 | 4.0 |
| Reference value, mg/dL | 191.1 ± 8.2 | 302.2 ± 30.7 |

As apparent from the data of Table 2, the differential flat type glucose sensor of the present invention was found to be accurate and precise as coefficients of variation were measured to be 5.5% and 4.0% for the normal serum and the abnormal serum, respectively.

The porous membrane built-in biosensors of the present invention, as described hereinbefore, are provided with sample inlets which can be introduced samples in a constant quantity and rate to the biosensors without pretreatment. In addition to being simple in structure, the biosensors of the present invention can be fabricated with ease and produced on mass production at low cost. Further to these, the biosensors of the present invention allow patients to detect blood levels of metabolites associated with various diseases accurately irrespective of interfering materials and by themselves. Therefore, the biosensors can find numerous applications in accurate and precise quantification apparatuses.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A biosensor with porous membranes, comprising:
   (a) a lower substrate;
   (b) an electrode layer patterned on the lower substrate;
   (c) a porous membrane formed on a portion of the electrode layer, defining an area for an at least one electrode;
   (d) an adhesive formed over a portion of the electrode layer not having the porous membrane, serving as an insulator;
   (e) an upper substrate having a hole, the upper substrate facing with the porous membrane; and
   (f) a second upper substrate containing a sample inlet for introducing samples through the hole to the biosensor, wherein either the at least one electrode or the porous membrane has an oxidase enzyme and an electron transfer mediator immobilized thereto, when a whole blood sample is introduced to the biosensor, the whole blood sample is separated into its components during the chromatographic motion through the porous membrane so that only blood plasma can be contacted with the electrode system.

2. The biosensor as set forth in claim 1, wherein said biosensor is a face-to-face type with a three-electrode system, comprising:
   (a) the lower substrate 10;
   (b) the electrode layer formed on the lower substrate 10, comprising a J-shaped working electrode connector strip 11' with a working electrode 11 established thereon, a counter electrode connector strip 12', and a reference electrode connector strip 13' with a reference electrode 13 established thereon;
   (c) the porous membrane 16 or the working electrode 11 having the oxidase enzyme and the electron transfer mediator immobilized thereto;
   (d) the adhesive 17 covered over a portion of the lower substrate 10 not having the porous membrane 16;
   (e) a Y-shaped circuit connector strip 20 with a counter electrode 12 on the branched line ends, and
   (f) the upper substrate 10', fixed by the adhesive 17, having the hole 18; and
   (g) the second upper substrate 10", fixed to the first upper substrate 10' via an adhesive 17, having the sample inlet 14, wherein the sample inlet has two opposite open ends through which samples are introduced to the biosensor.

3. The biosensor as set forth in claim 1, wherein said biosensor is a face-to-face type with a three-electrode system, comprising:
   (a) the lower substrate 10;
   (b) the electrode layer formed on the lower substrate 10, comprising a J-shaped working electrode connector strip 11' with a working electrode 11 established thereon, a counter electrode connector strip 12', and a reference electrode connector strip 13' with a reference electrode 13 established thereon;
   (c) the porous membrane 16 or the working electrode 11 having the oxidase enzyme and the electron transfer mediator immobilized thereto;
   (d) the adhesive 17 covered over a portion of the lower substrate 10 not having porous membrane 16;
   (e) a Y-shaped circuit connector strip 20 with a counter electrode 12 on the branched line ends, and
   (f) the upper substrate 10', via the adhesive 17, having the hole 18; and
   (g) the second upper substrate 10" with a second hole 18' fixed to the first upper substrate 10' via an adhesive 17, having the sample inlet 14 extending from a mid point to an end of the second upper substrate 10", wherein the sample inlet has one open end through which samples are introduced to the biosensor.

4. The biosensor as set forth in claim 1, wherein said biosensor is a face-to-face type employing a two-electrode system, comprising:
   (a) the lower substrate 10;
   (b) the electrode layer formed on the lower substrate 10, comprising a Y-shaped working electrode connector strip 11' with a working electrode 11 established thereon and a counter electrode connector strip 12' the latter it is connected to one end portion of a circuit connector strip 20 on the upper substrate 10';
   (c) the porous membrane 16 or the working electrode 11 having the oxidase enzyme and the electron transfer mediator immobilized thereto;
   (d) the adhesive 17 covered over a portion of the lower substrate 10 not having the porous membrane 16;
   (e) the Y-shaped circuit connector strip 20 with a counter electrode 12 on the branched line ends, and
   (f) the upper substrate 10', via the adhesive 17, having the hole 18; and
   (g) the second upper substrate 10", having the sample inlet, fixed to the first upper substrate 10' 14 via an adhesive 17, wherein the sample inlet has two opposite open ends through which samples are introduced to the biosensor.

5. The biosensor as set forth in claim 1, wherein said biosensor is a face-to-face type with a two-electrode system, comprising:

(a) the lower substrate 10;
(b) the electrode layer formed on the lower substrate 10, comprising a Y-shaped working electrode connector strip 11' with a working electrode 11 established thereon and a counter electrode connector strip 12' established thereon;
(c) the porous membrane 16 or the working electrode 11 having the oxidase enzyme and the electron transfer mediator immobilized thereto;
(d) the adhesive 17 covered over a portion of the lower substrate 10 not having the porous membrane 16;
(e) a Y-shaped circuit connector strip 20 with a counter electrode 12 on the branched line ends,
(f) the upper substrate 10', fixed by the adhesive 17, having the hole 18; and
(g) the second upper substrate 10" with a second hole of upper substrate 18', having the sample inlet 14, fixed to the first upper substrate 10' via an adhesive 17, wherein the sample inlet has one open end through which samples are introduced to the biosensor.

6. The biosensor as set forth in claim 1, wherein said biosensor is a face-to-face type employing a two-electrode system, all of the electrodes being made of carbon ink only, comprising:
(a) the lower substrate 10;
(b) the electrode layer formed on the lower substrate 10, comprising a Y-shaped working electrode connector strip 11' with a working electrode 11 established thereon and a counter electrode connector strip 12';
(c) the porous membrane 16 or the working electrode 11 having the oxidase enzyme and the electron transfer mediator immobilized thereto;
(d) the adhesive 17 covered over a portion of the lower substrate 10 not having the porous membrane 16;
(e) a Y-shaped circuit connector strip 20 with a counter electrode 12 on the branched line ends,
(f) the upper substrate 10', formed on the adhesive 17, having the hole 18; and
(g) the second upper substrate 10", having the sample inlet 14, fixed to the first upper substrate 10' via an adhesive 17, wherein the sample inlet has two opposite open ends through which samples are introduced to the biosensor.

7. The biosensor as set forth in claim 1, wherein said biosensor is a face-to-face type with a three-electrode system characterized by providing a circular space for a sample inlet, comprising:
(a) the lower substrate 10;
(b) the electrode layer formed on the lower substrate 10, comprising a J-shaped working electrode connector strip 11' with a working electrode 11 established thereon, a counter electrode connector strip 12', and a reference electrode connector strip 13' with a reference electrode 13 established thereon;
(c) the porous membrane 16 or the working electrode 11 having the oxidase enzyme and the electron transfer mediator immobilized thereto;
(d) the adhesive 17 covered over a portion of the lower substrate 10 not having the porous membrane 16;
(e) a Y-shaped circuit connector strip 20 with a counter electrode 12 on the branched line ends,
(f) the upper substrate 10', fixed by the adhesive 17, having the hole 18 through which samples are introduced inside the biosensor; and
(g) a circular second upper substrate 10" with a circular sample inlet 14, fixed to the upper substrate 10' via an adhesive 17.

8. The biosensor as set forth in claim 1, wherein said biosensor is a face-to-face type with a two-electrode system characterized by providing a circular space for a sample inlet, comprising:
(a) the lower substrate 10;
(b) the electrode layer formed on the lower substrate 10, comprising a J-shaped working electrode connector strip 11' with a working electrode 11 established thereon, a counter electrode connector strip 12', the latter it is connected to one end portion circuit connector strip 20 on the upper substrate 10';
(c) the porous membrane 16 or the working electrode 11 having the oxidase enzyme and the electron transfer mediator immobilized thereto;
(d) the adhesive 17 covered over a portion of the lower substrate 10 not having the porous membrane 16;
(e) the Y-shaped circuit connector strip 20 with a counter electrode 12 on the branched line ends,
(f) the upper substrate 10', fixed by the adhesive 17, having the hole 18 through which samples are introduced inside the biosensor; and
(g) a circular second upper substrate 10" with a circular sample inlet 14, fixed to the upper substrate 10' via an adhesive 17.

9. The biosensor as set forth in claim 1, wherein said biosensor is a flat type adopting a three-electrode system, comprising:
(a) the lower substrate 10;
(b) the electrode layer, formed on the lower substrate 10, comprising a working electrode connector strip 11' with a working electrode 11 established thereon, a counter electrode connector strip 12' with a J-shaped counter electrode 12 established thereon, and a reference electrode connector strip 13' with a reference electrode 13 established thereon;
(c) the porous membrane 16, formed on a predetermined area of the electrode layer, covering the working electrode 11, and the adhesive 17 deposited over a portion of the lower substrate not having the porous membrane 16;
(d) the upper substrate 10' with the hole 18 fixed to the lower substrate 10 via the adhesive 17; and
(e) the second upper substrate 10" with a second hole 18', having the sample inlet, fixed to the first upper substrate 10' 14 via an adhesive 17, wherein said sample inlet 14 is formed straightly extending from a mid point to one end of the second upper substrate 10" and is introduced samples to the biosensor.

10. The biosensor as set forth in claim 1, wherein said biosensor is a flat type employing a two-electrode system, comprising:
(a) the lower substrate 10;
(b) the electrode layer, formed on the substrate 10, consisting of a working electrode connector strip 11' with a working electrode 11 established thereon and a counter electrode connector strip 12' with a J-shaped counter electrode 12 established thereon;
(c) the porous membrane 16, formed on a predetermined area of the electrode system, covering the working electrode 11, and an adhesive 17 deposited over a portion of the lower substrate not having the porous membrane 16;

(d) the upper substrate 10' with the hole 18 fixed to the lower substrate 10 via the adhesive 17; and (e) the second upper substrate 10" with a second hole of 18', having the sample inlet 14, fixed to the first upper substrate 10' via an adhesive 17, wherein said a sample inlet 14 is formed straightly extending from a mid point to one end of the second upper substrate 10" and is introduced samples to the biosensor.

11. The biosensor as set forth in claim 1, wherein the porous membrane 16 contains pores ranging from 5 to 20 μm in diameter.

12. The biosensor as set forth in claim 1, wherein the porous membrane 16 is selected from paper, a hydrophilic organic polymer or a hygroscopic ceramic polymer.

13. The biosensor as set forth in claim 12, wherein a hydrophilic organic polymer or a hygroscopic ceramic polymer is selected from the group consisting of nylon, hydrophilic polyester sulfone membranes, hydrophilic mixed cellulose esters, polytetrafluoroethylene membranes, polyvinylidine fluoride membranes, ion-selective membranes, glass fiber, and polyester fiber or its modified fiber membranes.

14. The biosensor as set forth in claim 1, wherein the porous membrane 16 is selected from a group consisting of nitrocellulose paper, polyester fiber or its modified fiber membranes and filter paper.

15. The biosensor as set forth in claim 1, wherein the oxidase is selected from the group consisting of glucose oxidase, lactate oxidase, cholesterol oxidase, glutamate oxidase, horse radish peroxidase and alcohol oxidase.

16. The biosensor as set forth in claim 1, wherein the electron transfer mediator is selected from the group consisting of hexaamineruthenium (III) chloride, potassium ferricyanide, potassium ferrocyanide, dimethylferrocene (DMF), ferricinium, ferocene-monocarboxylic acid (FCOOH), 7,7,8,8-tetracyanoquinodimethane (TCNQ), tetrathiafulvalene (TTF), nickelocene (Nc), N-methylacidinium (NMA$^+$), tetrathiatetracene (TTT, N-methylphenazinium (NMP$^+$), hydroquinone, 3-dimethylaminobenzoic acid (MBTHDMAB), 3-methyl-2-benzothiozolinone hydrazone, 2-methoxy-4-allylphenol, 4-aminoantipyrine (AAP), dimethylaniline, 4-aminoantipyrene, 4-methoxynaphthol, 3,3',5,5'-tetramethylbenzidine (TMB), 2,2-azino-di-[3-ethylbenzothizoline sulfonate], o-dianisidine, o-toluidine, 2,4-dichloro phenol, 4-aminophenazone, benzidine, prussian blue as mixed-valence compounds capable of forming redox couples.

17. The biosensor as set forth in claim 1, wherein the substrate is formed of ceramic, plastic, silicon, alumina glass plates, or polymeric materials.

18. The biosensor as set forth in claim 1, further comprising a protective membrane 22 is formed of an organic polymer selected from the group consisting of polyester, polyvinyl chloride, and polycarbonate.

19. The biosensor as set forth in claim 1, wherein the at least one electrode is fabricated in a direct chemical vacuum deposition process or in a plasma deposition process.

20. The biosensor as set forth in claim 1, wherein the sample inlet 14 is modified with a surfactant or by additives to improve the mobility of the whole blood sample through the porous membrane.

21. The biosensor as set forth in claim 1, wherein the sample inlet 14 is modified in morphology and size by applying grooves to the sample inlet or the hole.

22. The biosensor as set forth in claim 1, wherein the pretreatment layer 19 is provided with a sample inlet for removing various interfering materials, whereby the quantification of samples of interest can be improved in measurement convenience, accuracy and precision.

23. A biosensor with porous membranes, wherein said biosensor is a differential face-to face type with a three-electrode system, comprising:

(a) a lower substrate 10;

(b) a plurality of spaced first circuit connectors; formed on the lower substrate 10, (c) a counter electrode 12 and a reference electrode 13, both being coated on the first circuit connectors 9 at predetermined regions;

(d) an insulator 15 covering the surface of the lower substrate 10 with the exception of a portion of the lower substrate containing the counter electrode 12 the reference electrode 13, and a terminal region of the lower substrate 10;

(e) a porous membrane 16 located on the counter electrode 12 and the reference electrode 13, the porous membrane 16 having the same dimension as the exposed portion of the counter electrode 12 and a reference electrode 13;

(f) an adhesive 17 deposited over the insulator 15

(g) a working electrode 11 atop the porous membrane 16;

(h) a second circuit connector 9' extending to the working electrode 11;

(i) upper substrate 10' covering second insulator 15' that exposes the working electrode 11;

(j) a plurality of differential circuit connectors 90 formed below the lower substrate 10;

(k) a differential counter electrode 120 and a differential reference electrode 130;

(l) a differential insulator 150 formed on the differential circuit connectors 90;

(m) a differential porous membrane 160;

(n) a differential adhesive 170 below the differential insulator 150;

(o) a differential working electrode 110 on the differential porous membrane 160;

(p) a second differential circuit connector 90 with the differential adhesive 170;

(q) a differential second insulator 150; and (r) a differential upper substrate 100, each of the differential elements of (i) through (r) functioning in the same manner as that of its corresponding elements of (a) through (j).

24. A biosensor with porous membranes, wherein said biosensor is a differential face-to-face type with a two-electrode system, comprising:

(a) a lower substrate 10;

(b) a plurality of spaced first circuit connectors 9; formed on the lower substrate 10, (c) a counter electrode 12 being coated on the first circuit connectors 9 at a predetermined region;

(d) an insulator 15 covering the surface of the lower substrate 10 exception of a portion of the lower substrate containing the counter electrode 12 and a terminal region of the lower substrate 10;

(e) a porous membrane 16 located on the counter electrode 12, having the same dimension as the exposed portion containing the counter electrode;

(f) an adhesive 17 deposited over the insulator 15;

(g) a working electrode 11 atop the porous membrane 16;

(h) a second circuit connector 9' extending to the working electrode 11;

(i) upper substrate 10' covering a second insulator 15' that exposes the working electrode 11;

(j) a plurality of differential circuit connectors 90 formed below the lower substrate 10;

(k) a differential counter electrode 120;

(l) a differential insulator 150 formed on the differential circuit connectors 90;

(m) a differential porous membrane 160;

(n) a differential adhesive 170 below the differential insulator 150;

(o) a differential working electrode 110 on the differential porous membrane 160;

(p) a second differential circuit connector 90 with the differential adhesive 170;

(q) a differential second insulator 150; and (r) a differential upper substrate 100, each of the differential elements of (j) through (r) functioning in the same manner as that of its corresponding elements of (a) through (i).

25. A biosensor with porous membranes, wherein said biosensor is a face-to-face type employing a two-electrode system, characterized in that the sample inlet 14 is formed in an upper substrate 10 not in a second upper substrate 10 and all electrodes are fabricated by carbon ink only, comprising:

(a) a lower substrate 10;

(b) an electrode layer formed on the lower substrate 10, comprising a Y-shaped working electrode connector strip 11 with a working electrode 11 established thereon and a counter electrode connector strip 12, all of the electrodes coated with carbon ink only;

(c) a porous membrane 16, formed on a predetermined area of the electrode layer, covering the working electrode 11;

(d) an adhesive 17 covered over a portion of the lower substrate 10 not having the porous membrane 16;

(e) a Y-shaped circuit connector strip 20 with a counter electrode 12 coated with carbon ink only, (f) an upper substrate 10, fixed by the adhesive 17, having a sample inlet 14 extending in the lengthwise direction to one end of the upper substrate 10 from a mid point and thus having an open end; and (g) a second upper substrate 10, fixed to the first upper substrate 10 via an adhesive 17, having a second hole of upper substrate 18.

26. A biosensor with porous membranes, wherein said biosensor is a flat type employing a three-electrode system, which has a porous membrane as a lower substrate, comprising:

(a) a lower substrate made of a porous membrane 16;

(b) an insulator 15 formed on one half portion of the lower substrate 16, an electrode system, formed on the insulator 15, comprising a working electrode connector strip 11 with a working electrode 11 established thereon, a counter electrode connector strip 12 with a counter electrode 12 established thereon, and a reference electrode connector strip 13 with a reference electrode 13 established thereon, and a pretreatment layer 19 adjacent to the insulator 15; and (c) an upper substrate 10 fixed onto the another half portion of the porous membrane 16 via an adhesive 17, having an sample inlet 14 which is formed in the direction traversing the electrode system and has two open ends, wherein through the sample inlet having two open ends, samples can be introduced from both the left and right ends of the biosensor adopting the three-electrode system.

27. A biosensor with porous membranes, wherein said biosensor is a flat type employing a two-electrode system, which has a porous membrane as a lower substrate, comprising:

(a) a lower substrate made of a porous membrane 16;

(b) an insulator 15 formed on one half portion of the lower substrate 16, an electrode system, formed on the insulator 15, comprising a working electrode connector strip 11 with a working electrode 11 established thereon and a counter electrode connector strip 12 with a counter electrode 12 established thereon and a pretreatment layer 19 adjacent to the insulator 15; and (c) an upper substrate 10 fixed onto the another half portion of the porous membrane 16 via an adhesive 17, having an sample inlet 14 which is formed in the direction traversing the electrode system and has two open ends, wherein through the sample inlet having two open ends, samples can be introduced from both the left and right ends of the biosensor adopting the three-electrode system.

* * * * *

UNITED STATES PATENT AND TRADEMARK OFFICE
CERTIFICATE OF CORRECTION

PATENT NO. : 6,726,818 B2
DATED : April 27, 2004
INVENTOR(S) : Gang Cui et al.

It is certified that error appears in the above-identified patent and that said Letters Patent is hereby corrected as shown below:

Column 20,
Line 61, after "inlet" insert -- 14 --.
Line 61, after "10•" delete "14".

Column 22,
Line 49, after the word "inlet" insert -- 14 --.
Line 50, after "10" delete "14".

Column 23,
Line 3, after "of" insert -- upper substrate --.

Column 24,
Line 47, delete "(i)" and insert -- (j) --.

Column 25,
Line 27, delete "10" and insert -- 10• -- (both occurrences).
Line 33, delete "11" and insert -- 11• --.
Line 34, delete "12" and insert -- 12• --.
Lines 43, 45 and 47, delete "10" and insert -- 10• --.

Column 26,
Lines 2, 18 and 37, delete "10" and insert -- 10• --.
Lines 12 and 34, delete "11" and insert -- 11• --.
Lines 13 and 35, delete "12" and insert -- 12• --.
Line 15, delete "13" and insert -- 13• --.

Signed and Sealed this

Eighteenth Day of October, 2005

JON W. DUDAS
*Director of the United States Patent and Trademark Office*